(12) United States Patent
Tsunamoto

(10) Patent No.: US 12,094,591 B2
(45) Date of Patent: Sep. 17, 2024

(54) MEDICAL IMAGE MANAGEMENT APPARATUS, MEDICAL IMAGE MANAGEMENT METHOD, AND RECORDING MEDIUM

(71) Applicant: KONICA MINOLTA, INC., Tokyo (JP)

(72) Inventor: Yuki Tsunamoto, Tachikawa (JP)

(73) Assignee: KONICA MINOLTA, INC., Tokyo (JP)

( * ) Notice: Subject to any disclaimer, the term of this patent is extended or adjusted under 35 U.S.C. 154(b) by 855 days.

(21) Appl. No.: 17/012,733

(22) Filed: Sep. 4, 2020

(65) Prior Publication Data

US 2021/0074409 A1    Mar. 11, 2021

(30) Foreign Application Priority Data

Sep. 5, 2019    (JP) .................................. 2019-162405

(51) Int. Cl.
| | |
|---|---|
| G16H 30/20 | (2018.01) |
| G06F 3/0482 | (2013.01) |
| G06F 16/51 | (2019.01) |
| G06F 21/62 | (2013.01) |
| G16H 15/00 | (2018.01) |
| G16H 30/40 | (2018.01) |
| G16H 40/20 | (2018.01) |

(52) U.S. Cl.
CPC ............. *G16H 30/20* (2018.01); *G06F 16/51* (2019.01); *G06F 21/6254* (2013.01); *G16H 15/00* (2018.01); *G16H 30/40* (2018.01); *G16H 40/20* (2018.01); *G06F 3/0482* (2013.01)

(58) Field of Classification Search
CPC ........ G16H 30/20; G16H 15/00; G16H 30/40; G16H 40/20; G06F 16/51; G06F 21/6254; G06F 3/0482; G06F 16/53; G06F 21/6245; A61B 6/463; A61B 6/566
USPC ........................................................ 705/2, 3
See application file for complete search history.

(56) References Cited

FOREIGN PATENT DOCUMENTS

| | | | | |
|---|---|---|---|---|
| JP | 2007330592 A | * | 12/2007 | ........... A61B 6/4494 |
| JP | 2008188329 A | * | 8/2008 | |

(Continued)

OTHER PUBLICATIONS

Kalender, W.A., Kyriakou, Y. Flat-detector computed tomography (FD-CT). Eur Radiol 17, 2767â2779 (2007). https://doi.org/10.1007/s00330-007-0651-9 (Year: 2007).*

(Continued)

*Primary Examiner* — Joshua B Blanchette
(74) *Attorney, Agent, or Firm* — CANTOR COLBURN LLP

(57) ABSTRACT

A medical image management apparatus including a hardware processor. The hardware processor retrieves image data from an image capturer that generates and stores the image data of a medical image, and in retrieving the image data that is generated by memory imaging and stored in the image capturer, the hardware processor disables automatic associating of the image data obtained by the memory imaging with at least one of patient information and order information or disables retrieving of the image data obtained by the memory imaging in a state in which the image data obtained by the memory imaging is automatically associated with at least one of the patient information and the order information.

24 Claims, 16 Drawing Sheets

(56) References Cited

FOREIGN PATENT DOCUMENTS

| | | |
|---|---|---|
| JP | 2009207509 A | 9/2009 |
| JP | 2016077541 A | 5/2016 |
| WO | WO-2010061700 A1 * | 6/2010 ............. G06F 19/00 |

OTHER PUBLICATIONS

JPO Notice of Reasons for Refusal for corresponding JP Application No. 2019-162405; Mailing Date, Feb. 14, 2023.

* cited by examiner

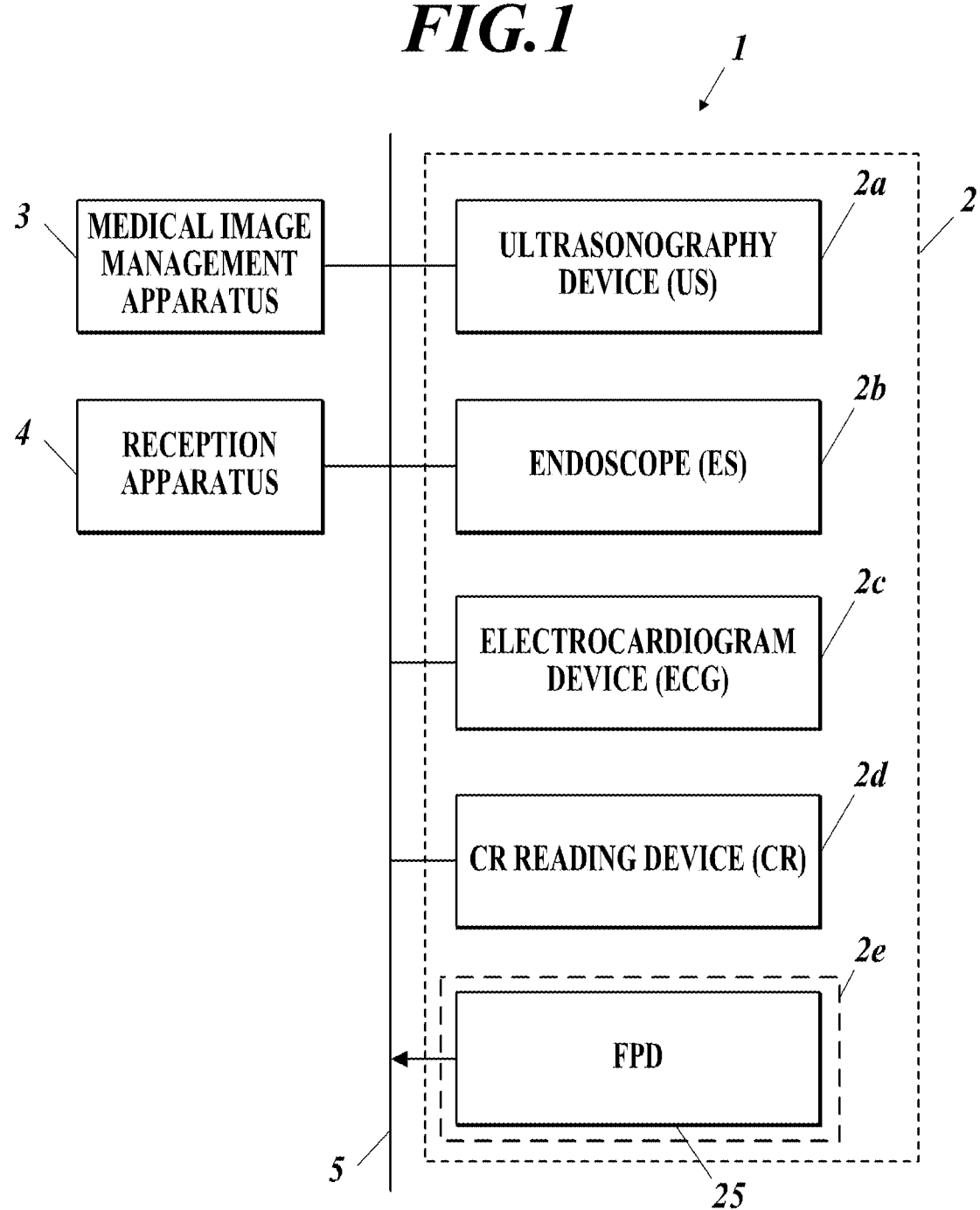

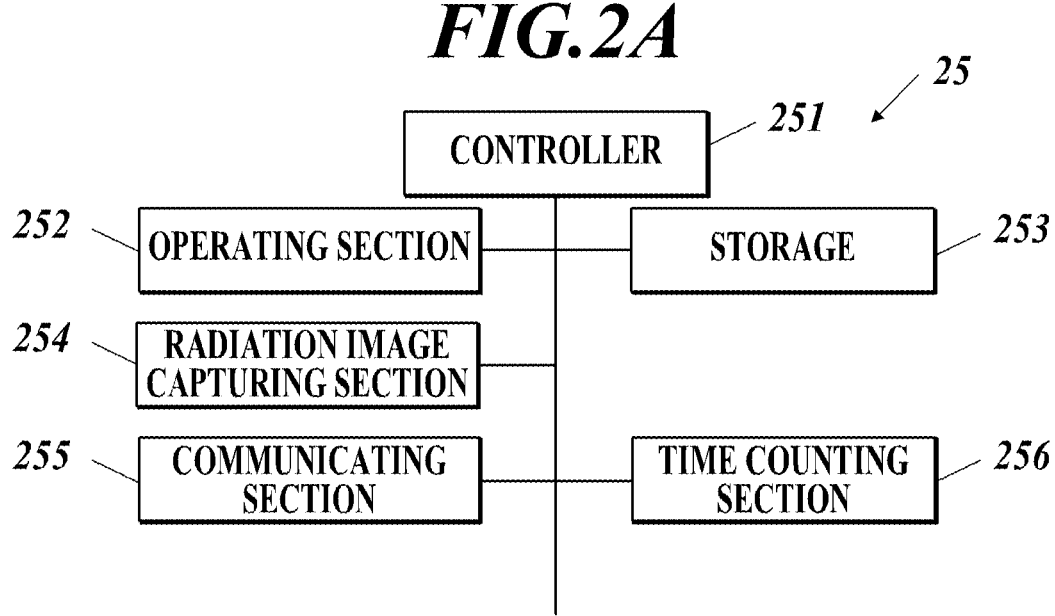
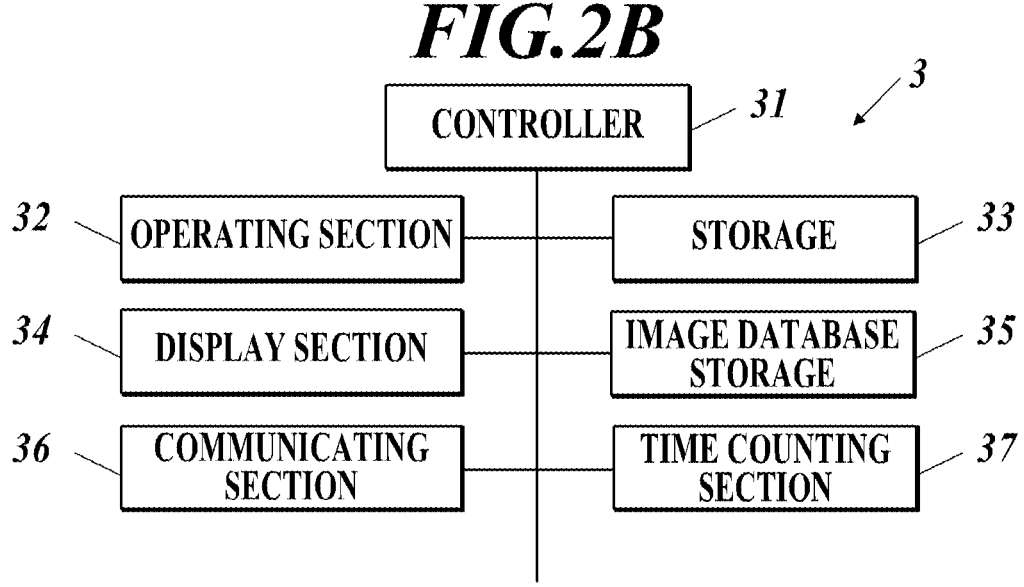

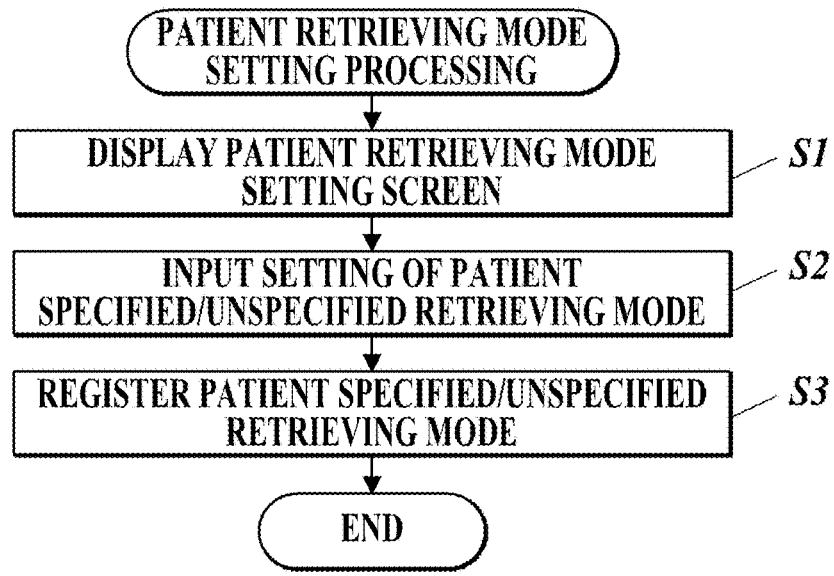
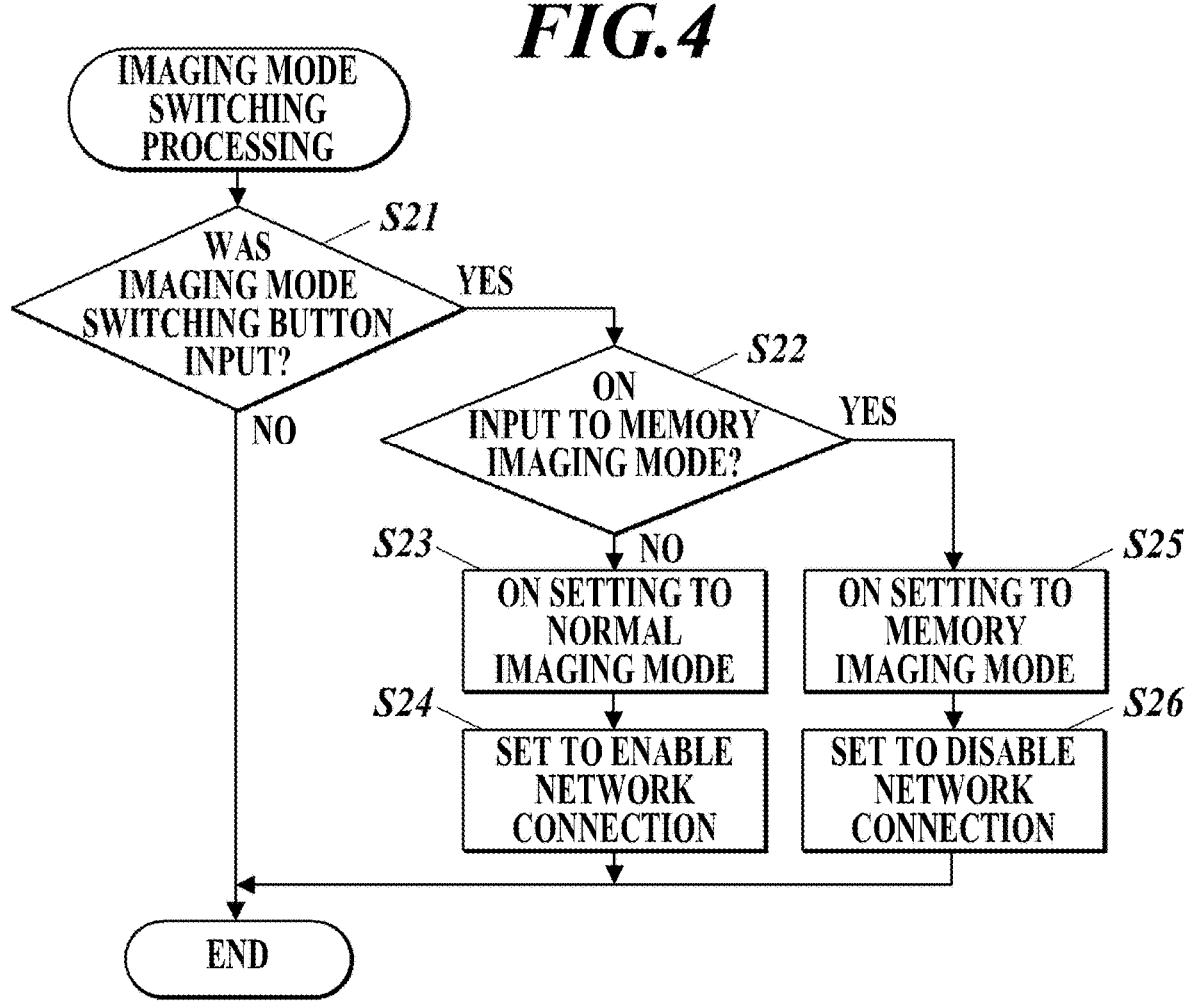

FIG.12

| RECEPTION | SEARCH | | | | | | | | | | | |
|---|---|---|---|---|---|---|---|---|---|---|---|---|
| START RECEPTION | | | | | | | ▽ △ | | LOGIN NAME | 01 0001 | | |

| BASIC INFORMATION | VITAL | EXAMINATION HISTORY | OTHERES |
|---|---|---|---|

PATIENT ID: 070330 0011
PATIENT NAME (KANA): ○○ ***
PATIENT NAME (KANJI): ○○ ***
PATIENT NAME (ASCII): ○○ Taro SEX: MALE
BIRTH DATE: *** AGE 17YEARS AND TWO MONTHS OLD
〒: *** ADDRESS SEARCH
ADDRESS: 16X-XXXX
PHONE NUMBER: 03-XXXX-XXXX
EMAIL ADDRESS: abcde@fgh.jp ATTENDING DOCTOR (KANJI): ***
Acession No.: ***

□ URGENCY □ URGENCY

TODAY'S COMMENTS (CONTENTS OF CONSULTATION):

PATIENT MEMO:

CORRECT    START RECEPTION    START EXAMINATION

PATIENT LIST

| ATTENDING DOCTOR | ALL ▽ | STATUS | ALL ▽ | DISPLAY ORDER | ASCENDING ORDER ▽ | UPDATE LIST |

| RECEPTION NUMBER | PATIENT ID | PATIENT NAME (KANA) | PATIENT NAME (KANJI) | SEX | AGE | RECEPTION TIME | WAITING TIME | PATIENT STATUS ICON | PATIENT STATUS | URGENCY | TODAY'S COMMENTS |
|---|---|---|---|---|---|---|---|---|---|---|---|
| 1 | 070330... | ○○ *** | ○○ *** | MALE | 17YEARS AND TWO MONTHS OLD | 11:33 | | | EXAMINED | | |
| 2 | 070330... | ○○ *** | ○○ *** | MALE | *** | 11:34 | 00:53 | 🕐 | WAITING FOR EXAMINATION | | |
| 3 | 070330... | ○○ *** | ○○ *** | MALE | *** | 11:34 | 00:57 | 🕐 | WAITING FOR EXAMINATION | | |

DELETE FROM LIST

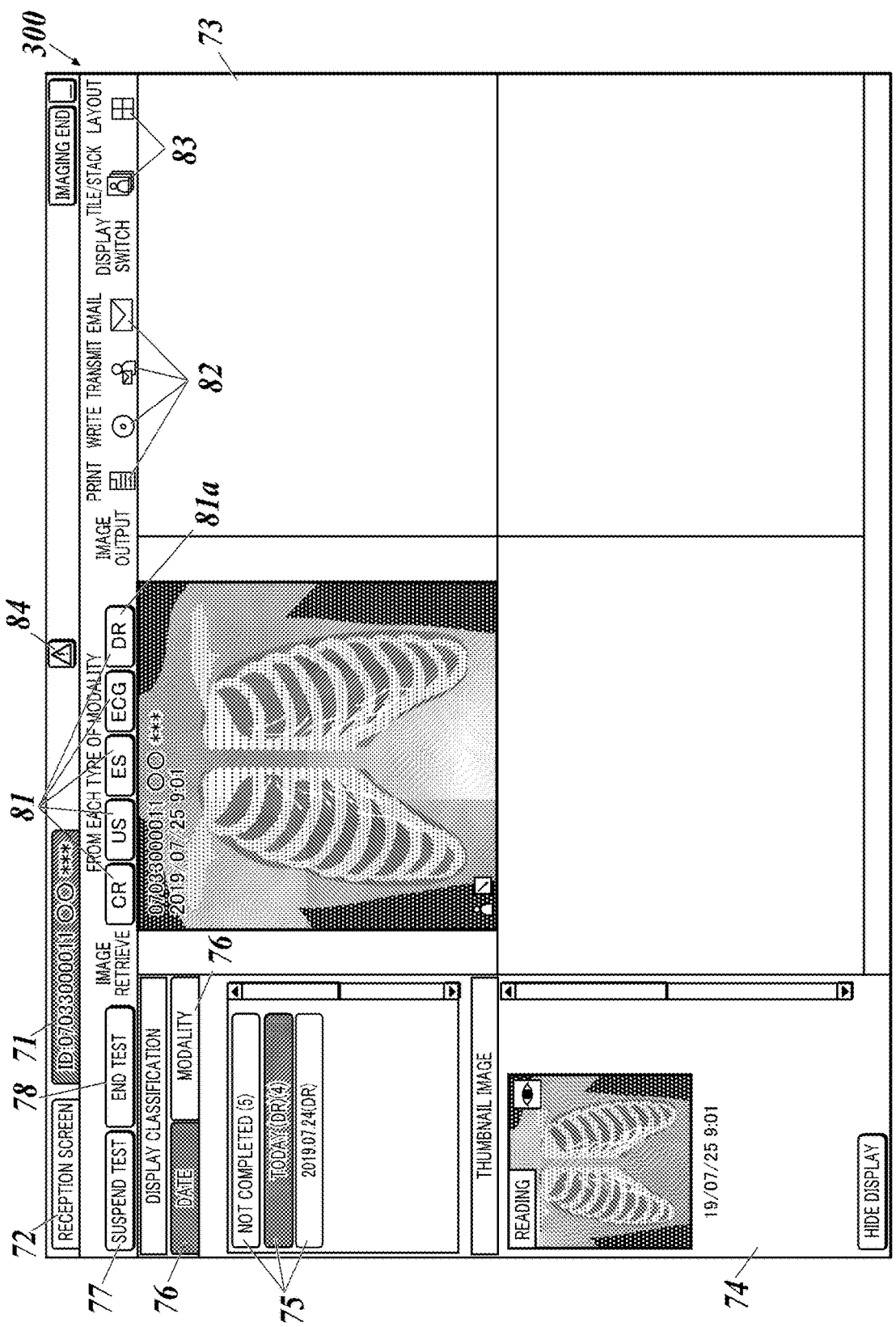

FIG.14

| MODALITY | IMAGE | IMAGING DATE AND TIME | SITE | PATIENT NAME (ASCII) | PATIENT NAME (KANA) | PATIENT NAME (KANJI) | SEX | BIRTH DATE | IMAGING METHOD |
|---|---|---|---|---|---|---|---|---|---|
| DR | | 2019/07/25 9:01:13 | | ○○ *** | | | | | MEMORY IMAGING |
| DR | | 2019/07/25 9:10:13 | | | | | | | MEMORY IMAGING |
| DR | | 2019/07/25 9:20:13 | | | | | | | MEMORY IMAGING |
| DR | | 2019/07/25 10:11:34 | | | | | | | MEMORY IMAGING |

PATIENT LIST

ATTENDING DOCTOR [ALL ▼]  STATUS [ALL ▼]  DISPLAY ORDER [ASCENDING ORDER ▼]  [UPDATE LIST]

| RECEPTION NUMBER | PATIENT ID | PATIENT NAME (KANA) | PATIENT NAME (KANJI) | SEX | AGE | RECEPTION TIME | WAITING TIME | PATIENT STATUS ICON | PATIENT STATUS | URGENCY | TODAY'S COMMENTS |
|---|---|---|---|---|---|---|---|---|---|---|---|
| 1 | 070330... | ○○ *** | ○○ *** | MALE | 17 YEARS AND TWO MONTHS OLD | 11:33 | | | EXAMINED | | |
| 2 | 070330... | ○○ *** | ○○ *** | MALE | *** | 11:34 | 00:53 | 🕐 | WAITING FOR EXAMINATION | | |
| 3 | 070330... | ○○ *** | ○○ *** | MALE | *** | 11:34 | 00:57 | 🕐 | WAITING FOR EXAMINATION | | |

[RETURN]

| MODALITY | IMAGE | IMAGING DATE AND TIME | SITE | PATIENT NAME (ASCII) | PATIENT NAME (KANJI) | PATIENT NAME (KANJI) | SEX | BIRTH DATE | IMAGING METHOD |
|---|---|---|---|---|---|---|---|---|---|
| DR | | 2019/07/25 9:10:13 | | | | | | | MEMORY IMAGING |
| DR | | 2019/07/25 9:20:13 | | | | | | | MEMORY IMAGING |

UNCONFIRMED IMAGE CHECK   SELECT PATIENT OF THIS IMAGE FROM LIST BELOW, AND DOUBLE CLICK   DELETE   CANCEL   LOGIN NAME

*220*

PATIENT LIST

ATTENDING DOCTOR [ALL]   STATUS [ALL]   DISPLAY ORDER [ASCENDING ORDER]   UPDATE LIST

| RECEPTION NUMBER | PATIENT ID | PATIENT NAME (KANA) | PATIENT NAME (KANJI) | SEX | AGE | RECEPTION TIME | WAITING TIME | PATIENT STATUS ICON | PATIENT STATUS | URGENCY | TODAY'S COMMENTS |
|---|---|---|---|---|---|---|---|---|---|---|---|
| 1 | 070330... | ○○ *** | ○○ *** | MALE | 17 YEARS AND TWO MONTHS OLD | 11:33 | | | EXAMINED | | |
| 2 | 070330... | ○○ *** | ○○ *** | MALE | *** | 11:34 | 00:53 | ⏲ | WAITING FOR EXAMINATION | | |
| 3 | 070330... | ○○ *** | ○○ *** | MALE | *** | 11:34 | 00:57 | ⏲ | WAITING FOR EXAMINATION | | |

*230*

RETURN

MEDICAL IMAGE MANAGEMENT APPARATUS, MEDICAL IMAGE MANAGEMENT METHOD, AND RECORDING MEDIUM

CROSS-REFERENCE TO RELATED APPLICATIONS

The present invention claims priority under 35 U.S.C. § 119 to Japanese Patent Application No. 2019-162405 filed on Sep. 5, 2019, the entire content of which is incorporated herein by reference.

BACKGROUND

Technological Field

The present invention relates to a medical image management apparatus, a medical image management method, and a recording medium.

Description of the Related Art

There has been conventionally known an image diagnosis system in which an operator such as a doctor and a technologist uses a DR (Digital Radiography) imaging device and an FPD (Flat Panel Detector) for a patient who visits a medical facility and performs radiation imaging (DR imaging) to the patient that is the test target, and the obtained image data of the radiation image is displayed and stored.

There has been also known a medical image management apparatus which specifies specific patient information in advance, and reads, from an image generation apparatus such as a CR (Computed Radiography) reading apparatus, image data obtained by imaging in the state of being associated with the patient, and thereby associates the image data with the patient information (see JP 2009-207509A). The medical image management apparatus can also retrieve the image data without specifying the patient information in advance and store the image data in an unconfirmed image region of an image database management section, and thereafter associate the patient information with the image data.

There has been also known an imaging system that determines whether an imaging section (sensor) similar to the FPD holds image data which is not yet transmitted, and if the imaging section holds the untransmitted image data, automatically associates the untransmitted image data with an imaging order, and when the associating is performed, allows the use of the sensor (see JP 2016-77541A).

There has been known memory imaging that is temporarily storing a plurality of pieces of image data in the storage of the FPD in X-ray imaging. According to this imaging method, it is possible to perform imaging of a plurality of patients in a facility or the like with a single FPD, and store the plurality of pieces of image data.

SUMMARY

In the medical image management apparatus of JP 2009-207509A, the image data which was retrieved when the image retrieving button is not pressed is temporarily saved as unconfirmed image data which is not associated with the patient information. However, since retrieving the image data as image data of a specific patient is also allowed, there has been a possibility that the image data is associated with wrong patient information, depending on the timing when the image retrieving button is pressed.

In the imaging system of JP 2016-77541A, when there is an imaging order, the order information is automatically associated with the image data. Thus, there has been a possibility that the image data is associated with wrong (imaging) order information.

When memory imaging is performed, there is a possibility that a plurality of pieces of image data of a plurality of patients are stored in the FPD. Thus, when the image data is retrieved, there is a possibility that the image data of the plurality of patients is collectively retrieved from the FPD. Thus, in the medical image management apparatus of JP 2009-207509A, when specific patient information is specified in advance and then the image data is retrieved in the state of being associated with the patient, there has been a possibility that image data of a different patient is associated with the specified patient information when the image data of the different patient is left in the FPD.

An object of the present invention is to prevent image data from being associated with at least one of patient information and order information which is wrong.

To achieve at least one of the abovementioned objects, according to an aspect of the present invention, a medical image management apparatus reflecting one aspect of the present invention is a medical image management apparatus including a hardware processor that: retrieves image data from an image capturer that generates and stores the image data of a medical image; and in retrieving the image data that is generated by memory imaging and stored in the image capturer, disables automatic associating of the image data obtained by the memory imaging with at least one of patient information and order information or disables retrieving of the image data obtained by the memory imaging in a state in which the image data obtained by the memory imaging is automatically associated with at least one of the patient information and the order information.

To achieve at least one of the abovementioned objects, according to another aspect of the present invention, a medical image management apparatus reflecting one aspect of the present invention is a medical image management apparatus including a hardware processor that: retrieves image data from an image capturer that generates and stores the image data of a medical image; and in a state in which the image data is to be retrieved without specifying patient information of a patient or order information of imaging, disables retrieving the image data from the image capturer to automatically associate the image data with at least one of the patient information and the order information that is currently specified.

To achieve at least one of the abovementioned objects, according to another aspect of the present invention, a medical image management method reflecting one aspect of the present invention is a medical image management method including: retrieving that is retrieving image data from an image capturer which generates and stores the image data of a medical image; and controlling that is, in retrieving the image data which is generated by memory imaging and stored in the image capturer, disabling automatic associating of the image data obtained by the memory imaging with at least one of patient information and order information or disables retrieving of the image data obtained by the memory imaging in a state in which the image data obtained by the memory imaging is automatically associated with at least one of the patient information and the order information.

To achieve at least one of the abovementioned objects, according to another aspect of the present invention, a medical image management method reflecting one aspect of the present invention is a medical image management method including: retrieving that is retrieving image data from an image capturer which generates and stores the image data of a medical image; and controlling that is, in a state in which the image data is to be retrieved without specifying patient information of a patient or order information of imaging, disabling retrieving the image data from the image capturer by the retrieving to automatically associate the image data with at least one of the patient information and the order information which is currently specified.

To achieve at least one of the abovementioned objects, according to another aspect of the present invention, a recording medium reflecting one aspect of the present invention is a non-transitory recording medium storing a computer readable program causing a computer to function as: a retriever that retrieves image data from an image capturer which generates and stores the image data of a medical image; and a controller that, in retrieving the image data which is generated by memory imaging and stored in the image capturer, disables automatic associating of the image data obtained by the memory imaging with at least one of patient information and order information or disables retrieving of the image data obtained by the memory imaging in a state in which the image data obtained by the memory imaging is automatically associated with at least one of the patient information and the order information.

To achieve at least one of the abovementioned objects, according to another aspect of the present invention, a recording medium reflecting one aspect of the present invention is a non-transitory recording medium storing a computer readable program causing a computer to function as: a retriever that retrieves image data from an image capturer which generates and stores the image data of a medical image; and a controller that, in a state in which the image data is to be retrieved without specifying patient information of a patient or order information of imaging, disables retrieving the image data from the image capturer to automatically associate the image data with at least one of the patient information and the order information which is currently specified.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 1 is a block diagram showing the configuration of a medical image management system in an embodiment of the present invention;

FIG. 2A is a block diagram showing the functional configuration of FPD;

FIG. 2B is a block diagram showing the functional configuration of a medical image management apparatus;

FIG. 3 is a flowchart showing patient retrieving mode setting processing;

FIG. 4 is a flowchart showing imaging mode switching processing;

FIG. 12 is a reception screen;

FIG. 13 is a patient screen;

FIG. 14 is a view showing a first patient image associating screen;

FIG. 15 is a view showing a second patient image associating screen;

FIG. 16 is a view showing a third patient image associating screen;

FIG. 17 is a view showing a fourth patient image associating screen;

FIG. 18 is a view showing a fifth patient image associating screen; and

FIG. 19 is a view showing a sixth patient image associating screen.

DETAILED DESCRIPTION OF EMBODIMENTS

Figure 5:
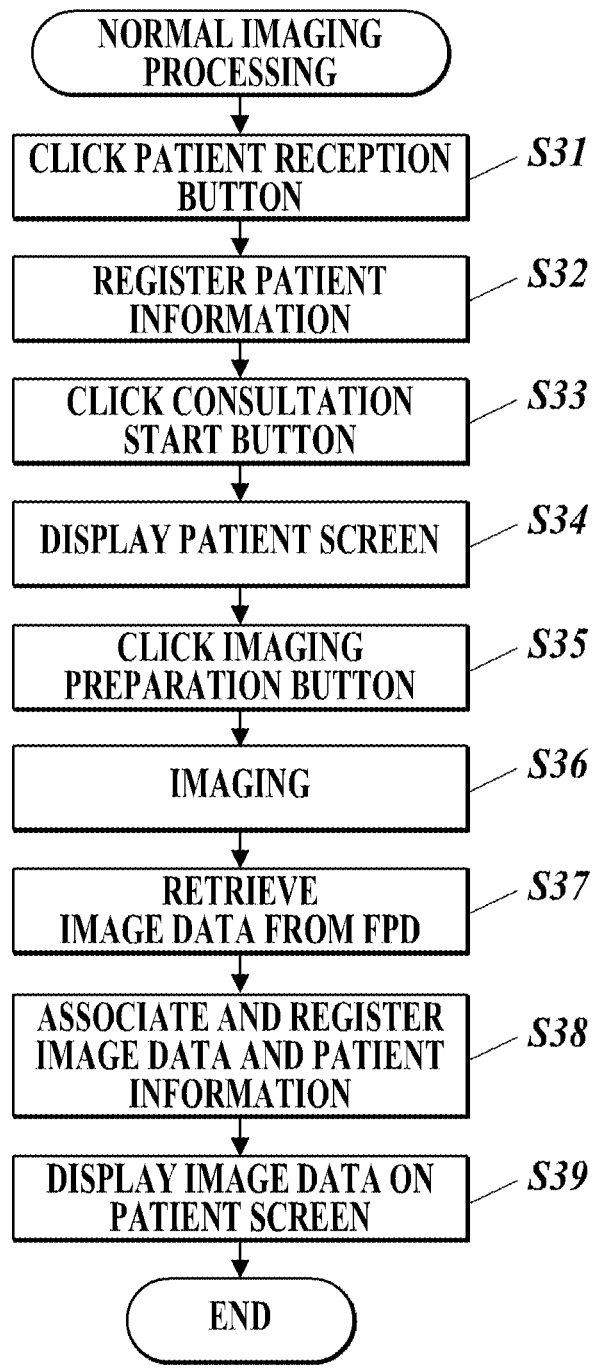
FIG. 5 is a flowchart showing normal imaging processing.

Hereinafter, one or more embodiments of the present invention will be described in detail with reference to the drawings. However, the scope of the invention is not limited to the disclosed embodiments or illustrated examples.

In the present embodiment, the medical image includes an X-ray image, an MRI image and a CT image, or may be icons thereof.

The image data is image data of the medical image obtained by imaging. The image data may include accompanying information having various types of information (such as patient information) related to the image data.

The patient information widely includes information specifying a patient. The patient information includes a patient ID, a patient name (kanji (Chinese characters), kana (Japanese phonetic characters), and ASCII), a sex, birth date, an age and the like of the patient.

The order information widely includes information related to imaging of the medical image, which was determined by questioning and history taking performed to the patient, or the like. The order information includes items such as the patient ID, the patient name, a site in the body of the patient to be imaged and an imaging direction, a device (modality) to be used, and the like.

The patient image associating screen is a screen for associating image data which was retrieved into the medical image management apparatus with at least one of the patient information and the order information. In the patient image associating screen, the image data and at least one of the patient information and the order information are displayed.

The list information widely includes information in a list form. Preferably, the image data is displayed as list information (image list) in the patient image associating screen. Similarly, the patient information is displayed as list information (patient list) in the patient image associating screen, and the order information is displayed as list information (order list) in the patient image associating screen. The patient image associating screen is automatically displayed in response to the completion of retrieving of the image data.

The completion of retrieving is a timing when at least one piece of image data was retrieved into the medical image management apparatus. The completion of retrieving may be a timing when part of the image data was retrieved into the medical image management apparatus. That is, at the time of completion of retrieving, image data not retrieved may remain in the image capturer. The completion of retrieving may be a timing when all pieces of image data were retrieved into the medical image management apparatus. In this case, the completion of retrieving is determined by that no image data remains in the image capturer.

In the embodiment, image data which was generated by the memory imaging and stored in the image capturer includes image data which was captured (imaging was performed) and generated in a memory imaging mode, image data which was captured and generated in a setting in which the image data is not to be transmitted from the image capturer to the medical image management apparatus, image data which was captured and generated in a state in which the network is disconnected and the image data cannot be transmitted, image data which was captured and generated in a setting in which the image data is not to be received by the medical image management apparatus, and the like. The image data may be recognized as image data which was generated by the memory imaging and stored in the image capturer, by a console inputting the information indicating the memory imaging in a tag of the image data (for example, DICOM image) and by the medical image management apparatus recognizing the tag information. The image data may be recognized as image data which was generated by the memory imaging and stored in the image capturer, by the medical image management apparatus performing image recognition of recognizing the image data which was captured in a state in which the memory imaging is indicated by using a marker (such as a lead marker). The image data may be recognized as image data which was generated by the memory imaging and stored in the image capturer when, for the image data retrieved by a retriever, at least one of time differences is a predetermined time or more or the operation time is after the imaging time, the time differences being a time difference between imaging time and retrieving time, a time difference between patient specifying time when the patient was specified and the imaging time or the retrieving time, a time difference between disconnection time when the image capturer disconnected the communication and the imaging time or the retrieving time, and a time difference between imaging time of previous image data for which imaging was performed before imaging of the image data and present imaging time of the image data which was retrieved this time, and the operation time being time when the image retrieving button is operated, or the patient information selection or the order information selection is operated.

With reference to FIG. 1, FIG. 2A and FIG. 2B, the apparatus configurations of a medical image management system 1 in the present embodiment will be described. FIG. 1 is a block diagram showing the system configuration of the medical image management system 1. FIG. 2A is a block diagram showing the functional configuration of an FPD 25. FIG. 2B is a block diagram showing the functional configuration of a medical image management apparatus 3.

The medical image management system 1 is a system which is applied in a relatively small medical facility such as a medical practitioner and a clinic. The medical facility is a facility which has a small number of hospital beds, but has hospital rooms for hospitalization. As shown in FIG. 1, the medical image management system 1 includes: an image generation apparatus 2; a medical image management apparatus 3, and a reception apparatus 4. The image generation apparatus 2 includes a DR reading device 2e including the FPD 25 as the image capturer. The image generation apparatus 2 may include an ultrasonography (US: UltraSonography) device 2a, an endoscope (ES: EndoScope) 2b, an electrocardiogram (ECG: ElectroCardioGram) device 2c, a CR reading device 2d, and the like. The medical image management apparatus 3 may be a medical image processing apparatus. Both of the FPD 25 and the DR reading device 2e in the present embodiment can be regarded as an image capturer.

The image generation apparatus 2 is not limited to the configuration of FIG. 1. The image generation apparatus 2 may include, for example, a CT (CT: Computed Tomography) imaging device, a magnetic resonance imaging (MRI: magnetic resonance imaging) device, and a digital camera imaging the outward appearance of the body such as a skin. The medical image management system 1 may include a plurality of image generation apparatuses 2 of a same type by including two DR reading devices 2e, for example. The combination of the image generation apparatuses 2 provided in the medical image management system 1 is not limited to the above combination.

The image generation apparatus 2, the medical image management apparatus 3 and the reception apparatus 4 are connected to a communication network 5 such as a LAN (Local Area Network) via a switching hub not shown in the drawings, for example. The communication network 5 particularly includes an access point for performing wireless communication connection with the FPD 25. The medical image management apparatus 3 is an information processing apparatus such as a work station provided in a consultation room where the doctor always stays. The medical image management apparatus 3 has a function of controlling activation and processing conditions of the image generation apparatus 2, a function of obtaining image data from the image generation apparatus 2 and displaying the image data so as to be associated with patient information, and a function as PACS (Picture Archiving and Communication Systems) which store and manage the image data associated with the patient information.

As the communication method in the hospital, DICOM (Digital Image and Communication in Medicine) standard is generally used. In the communication between apparatuses which are LAN connected, DICOM MWM (Modality Worklist Management) and DICOM MPPS (Modality Performed Procedure Step) are used. The communication method applicable to the present embodiment is not limited to this. The apparatuses which are LAN connected may include an apparatus not corresponding to the DICOM standard.

The medical facility in which the medical image management system 1 is installed includes, for example, a reception desk, a waiting room, a consultation room, a radiation imaging room, a test room and hospital rooms for hospitalized patients. The reception apparatus 4 is arranged at the reception desk. The medical image management apparatus 3 and the ultrasonography device 2a are arranged in the consultation room. The CR imaging device (not shown in the drawings), the CR reading device 2d, the DR imaging device (not shown in the drawings), and the DR reading device 2e are arranged in the radiation imaging room. The CR imaging device is a device which emits radiation to the CR cassette via the patient as a subject, to record a radiation image. The DR imaging device is a device which exposes the FPD 25 to radiation via the patient as the subject, to generate and store radiation image data. The medical image management apparatus 3 also functions as a console of the DR imaging device, and is connected to the DR imaging device via the communication network 5. The endoscope 2b and the electrocardiogram device 2c are arranged in the test room.

A person in charge is arranged at the reception desk in the medical facility. The person in charge provides a reception number tag, on which a reception number for identifying each individual person in the reception order is printed, to the patient who visited for consultation. The person in charge asks the patient name and inputs the association between the reception number and the patient name in the reception apparatus 4.

The patient after reception standbys in the waiting room, and enters the consultation room when the patient is called by the doctor. The medical image management apparatus 3 is set on the desk for consultation in the consultation room, and the medical image management apparatus 3 displays the image data imaging the (imaging) site of the diagnosis target of the patient, the test result related to the test performed to the patient, and the like. The ultrasonography device 2a which does not highly need to be used in an isolated space from the viewpoint of privacy or the like is also installed in the consultation room.

At the time of consultation by the doctor in the consultation room, there are performed, as needed, radiation imaging by the CR imaging device and the CR reading device 2d, radiation imaging by the DR imaging device and the DR reading device 2e, ultrasonic imaging by the ultrasonography device 2a, endoscope imaging by the endoscope 2b, and electrocardiogram recording by the electrocardiogram device 2c. The obtained image data is displayed on the medical image management apparatus 3 and stored to be associated with the patient information.

As described above, the image generation apparatus 2 is a modality which performs imaging to the imaging site of the patient as the subject, performs digital conversion of the captured image to generate image data of the captured image, and records a predetermined test result and generates image data.

The ultrasonography device 2a includes an ultrasonic probe (not shown in the drawings) which outputs ultrasonic waves, and an ultrasonography device body (not shown in the drawings) which is connected to the ultrasonic probe and converts the ultrasonic waves (echoes) received by the ultrasonic probe into the image data of the captured image of the internal structure. The ultrasonography device 2a transmits the ultrasonic waves into the body from the ultrasonic probe, receives the sound waves (echo signals) reflected at the structure inside the body with the ultrasonic probe, and generates, with the ultrasonography device body, the digital ultrasonic image data corresponding to the echo signals.

In the present embodiment, the ultrasonography device 2a has a function of providing the image data with accompanying information corresponding to the image data in the medical image management system 1 in a form based on the DICOM standard. The accompanying information is configured by including identification information of the image generation apparatus 2, the number indicating the imaging date and time, and the like.

The ultrasonography device 2a includes an input section (not shown in the drawings) such as a keyboard including character input keys and numerical input keys, and functions as an inputter to input patient information specifying the patient that is the imaging target. In the present embodiment, the patient information widely includes information specifying the patient including the patient ID, the patient name (kanji, kana, ASCII), the sex, the birth date and the age of the patient. Among them, the patient information input in the ultrasonography device 2a is the patient ID, the patient name, the sex and the birth date, for example. It is not necessary to input all of them in the ultrasonography device 2a, and the ultrasonography device 2a may be configured not to input any of the patient information.

The endoscope 2b has a compact imaging device at the tip of a tube having flexibility (none of them shown in the drawings). The imaging device includes, for example, an objective optical system which is configured by including optical lens, an image capturing section which is arranged at an imaging position of the objective optical system, and an illuminating section which is configured by including an LED (Light Emitting Diode) and performs illuminating necessary for performing the image capturing (none of them shown in the drawings). The image capturing section includes, for example, a solid-state image capturing element such as a CCD (Charge Coupled Device) and a CMOS (Complementary Metal-OxideSemiconductor), and performs photoelectric conversion into electrical signals of the amount corresponding to the incident light amount when the light enters. The objective optical system is configured to concentrate the light in the region illuminated by the illuminating section with the optical lens, and perform the imaging on the solid-state image capturing element included in the image capturing section. By the light entering the solid-state image capturing element being converted by the photoelectric conversion, the image data of the captured image is output as an electrical signal.

The electrocardiogram device 2c detects the electrocardiographic waveform, and obtains and records the waveform data. The electrocardiogram device 2c transmits the generated image data (waveform data) to the medical image management apparatus 3.

The CR reading device 2d reads image data from a CR cassette (not shown in the drawings) which is a radiation image conversion medium in which radiation image information obtained by imaging the imaging site of the patient is recorded. The CR cassette includes, for example, a built-in radiation image conversion plate including photostimulable phosphor sheet to accumulate radiation energy. When imaging is performed, the CR reading device 2d is arranged in the exposure region of radiation emitted from a radiation source (not shown in the drawings) of the CR imaging device. In the CR cassette, when radiation is emitted, the radiation of the amount following the radiation transmissivity distribution of the imaging site is accumulated on the photostimulable phosphor layer of the photostimulable phosphor sheet, and radiation image information of the imaging site is recorded on the photostimulable phosphor layer.

When the CR cassette having the radiation image information of the imaging site recorded therein is mounted, the CR reading device 2d emits excitation light to the photostimulable phosphor sheet in the CR cassette mounted in the CR reading device 2d, thus performs photoelectric conversion of the photostimulable light emitted from the sheet, performs A/D conversion of the obtained image signal, and generates the radiation image data of the captured image. The CR reading device 2d may be an integrated type device which is integrated with the CR imaging device.

The DR reading device 2e is a device which reads image data of the radiation image from an after-mentioned storage 253 of the FPD 25 which is the radiation image conversion medium in which the radiation image information obtained by imaging the imaging site is recorded. The DR reading device 2e in the present embodiment is the FPD 25. The FPD 25 generates image data of the radiation image corresponding to the X-ray emitted via the imaging site of the subject, and stores the generated image data with the accompanying information thereof.

The DR imaging includes normal imaging and memory imaging. The normal imaging is the imaging method of setting the FPD 25 on the imaging table of the DR imaging device via the subject in the radiation imaging room, performing one-by-one radiation imaging on the imaging table on which the subject is placed to generate the image data of the radiation image, storing the generated image data and the accompanying information one by one in the FPD 25, and retrieving the data into the medical image management apparatus 3. The memory imaging is the imaging method of using an X-ray device (not shown in the drawings) for doctor's rounds for check as the imaging (doctor's rounds for check) at the hospital room, generates image data of the radiation image by performing radiation imaging of at least one image for each of at least one person in the hospital room such as a patient who cannot walk easily to the radiation imaging room, for example, temporarily saving a plurality of pieces of image data and accompanying information in the FPD 25, and with a time interval after the imaging, collectively retrieving the plurality of pieces of image data and the accompanying information stored in the FPD 25 into the medical image management apparatus 3. In the memory imaging, it is not essential to carry the console (including portable terminal) to the hospital room in addition to the X-ray device for doctor's rounds for check.

When the imaging mode is set to the normal imaging mode of performing the normal imaging, the FPD 25 can be connected to the communication network 5. When the imaging mode is set to the memory imaging mode of performing the memory imaging, the FPD 25 is disabled from connecting to the communication network 5.

The endoscope 2*b*, the electrocardiogram device 2*c*, and the CR reading device 2*d* include a function of providing accompanying information to the generated image data. The endoscope 2*b* and the electrocardiogram device 2*c* include an operating section (not shown in the drawings) such as a keyboard including character input keys and numeric input keys, and allows input of patient information for specifying the patient that is the imaging target. The patient information which is input at the operating section of each of the devices is not particularly limited, and the patient information may not be input. When the device is configured to input only the patient ID as the patient information, the operating section may be a numeric keypad, for example. The information which was input is the accompanying information accompanying the image data of the captured image which was generated in each of the devices of the image generation apparatus 2.

The image data transmitted from each of the ultrasonography device 2*a*, the endoscope 2*b* and the electrocardiogram device 2*c* is DICOM image data based on the DICOM standard. The accompanying information may be or may not be attached to the DICOM image data. The image data generated by the CR reading device 2*d* and the DR reading device 2*e* is raw image data not based on the DICOM standard, and the image data is transmitted to the medical image management apparatus 3 without having patient information such as the patient ID attached thereto.

As shown in FIG. 2A, the FPD 25 includes a controller 251, an operating section 252, a storage 253, a radiation image capturing section 254, a communicating section 255 and a time counting section 256. The components in the FPD 25 are connected to each other via a bus.

The controller 251 is configured by including a CPU (Central Processing Unit), a RAM (Random Access Memory), and the like. The CPU of the controller 251 reads out system programs and various types of processing programs stored in the storage 253 and loads them into the RAM, and in accordance with the loaded programs, controls the components in the FPD 25.

The operating section 252 is configured by including an imaging mode switching button of receiving the switching input of the normal imaging mode and the memory imaging mode. The operating section 252 receives the operation input from the operator, and outputs the operation information to the controller 251.

The storage 253 is configured by including a nonvolatile semiconductor memory such as a flash memory, and stores various programs and various types of data executed by the controller 251. Particularly, the storage 253 stores the image data of the radiation image generated by the radiation image capturing section 254 and its accompanying information, and the imaging mode switching program for executing after-mentioned imaging mode switching processing. The image data and the accompanying information which were retrieved by the medical image management apparatus 3 are deleted after retrieving.

The radiation image capturing section 254 is configured by including an image capturing element such as a CMOS (Complementary Metal Oxide Semiconductor) image sensor which directly converts radiation into electrical signals as a direct conversion method, or configured by including, as an indirect conversion method, a phosphor such as gadolinium sulfate and cesium iodide and an image capturing element such as a photodiode which obtains, as electric charges, light which was generated by excitation of the phosphor with the incident radiation. The radiation image capturing section 254 generates image data of the radiation image with the image capturing element according to the radiation which was emitted through the subject and outputs and stores the generated image data in the storage 253, in accordance with the control by the controller 251.

The communicating section 255 is a wireless communicating section which includes an antenna, a modulation/demodulation section, a signal processing section and the like, and performs wireless communication with the DR reading device 2*e* and an external device such as the console of the X-ray device for doctor's rounds for check by the wireless LAN communication method. The controller 251 performs wireless communication with the external device such as the medical image management apparatus 3 via the communication network 5 with the communicating section 255. The communicating section 255 may be configured to perform wired communication with external devices in the communication network 5.

The time counting section 256 is a real time clock, and counts the current date and time and outputs the counted current date and time information to the controller 251.

The FPD 25 includes a battery not shown in the drawings such as a secondary cell which supplies electric power of power source to each component in the FPD 25.

As shown in FIG. 2B, the medical image management apparatus 3 includes a controller 31 (hardware processor) as a retriever, a controller and a setter, an operating section 32, a storage 33, a display section 34 as a display, an image database storage 35, a communicating section 36, and a time counting section 37. The components of the medical image management apparatus 3 are connected to each other via a bus.

The controller 31 is configured by including a CPU and a RAM. The controller 31 loads a specified program among the system programs and application programs stored in the storage 33 to the RAM, and executes various type of processing by the cooperation between the loaded program and the CPU.

The operating section 32 includes a keyboard including character input keys, numeral input keys and various types of function keys, and a pointing device such as a mouse. The operating section 32 outputs the key pressing signal operated via the keyboard by an operator such as a doctor and a technologist and the position operation signal by the mouse to the controller 31.

The storage 33 is configured by including an HDD (Hard Disk Drive), an SSD (Solid State Drive) and a semiconductor nonvolatile memory. The storage 33 stores various types of programs, and various types of data such as an image processing parameter (lookup table defining tone curve used in tone processing, emphasis degree of frequency processing, and the like) for adjusting the image data of the captured image to the image quality appropriate for diagnosis. The various types of programs include a patient retrieving mode setting program for performing after-mentioned patient retrieving mode setting processing, a remaining image patient specified retrieving setting program for performing remaining image patient specified retrieving setting processing, a normal imaging program for performing normal imaging processing, and a patient image associating program for performing patient image associating processing.

The display section 34 includes, for example, a display panel such as an LCD (Liquid Crystal Display) and an EL (ElectroLuminescence) display, and displays various screens in accordance with the instruction of display signal input from the controller 31. A touch panel may be formed on the display panel of the display section 34 as the operating section 32 to receive the touch input from the operator and output the touch operation signal to the controller 31.

The image database storage 35 is configured by including an HDD, an SSD or the like, and saves the image data of the captured image as the image database in association with the patient information.

The communicating section 36 is configured by including a network interface or the like, and performs transmission/reception of information with each of the devices in the image generation apparatus 2 and the reception apparatus 4 connected to the communication network 5 via a switching hub.

The time counting section 37 is a real time clock, and counts the current date and time and outputs the counted current date and time information to the controller 31.

The reception apparatus 4 is an information processing apparatus for performing reception registration, accounting calculation, insurance point calculation and the like of the patient who visited the hospital. The reception apparatus 4 includes: a controller which is configured by including a CPU and a RAM; an operating section which is configured by including a keyboard and a mouse; a storage which is configured by including an HDD; a display section which is configured by including an LCD; and a communicating section which performs communication with each apparatus connected to the communication network 5. When displaying of the reception input screen is instructed from the operating section, the reception apparatus 4 displays the reception input screen on the display section by software processing in cooperation between the CPU and the program stored in the storage. When reception information (reception number and patient name) is input from the input section via the reception input screen, the reception apparatus 4 creates (updates) a patient information list of the received patient, stores the list in the storage, and transmits the list to the medical image management apparatus 3 by the communicating section as needed.

Figure 6:
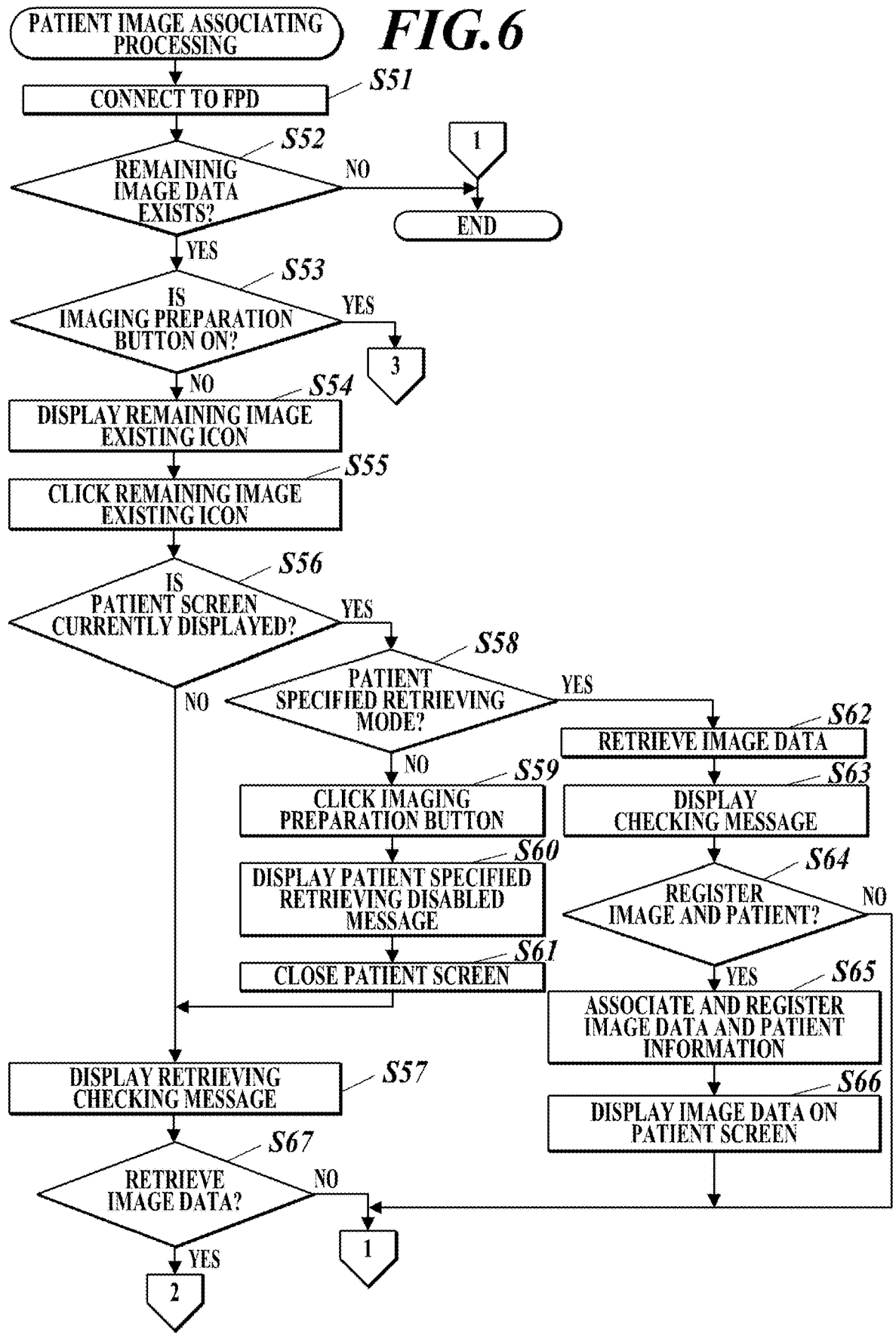
FIG. 6 is a flowchart showing patient image associating processing.
Figure 7:
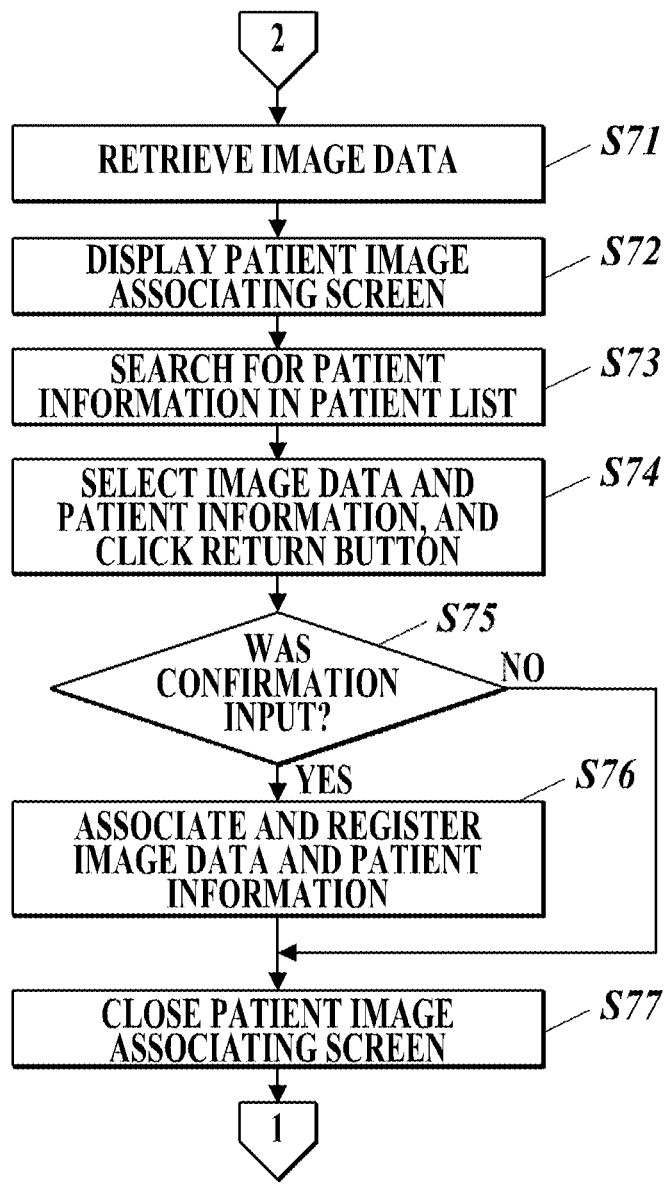
FIG. 7 is a flowchart showing the patient image associating processing following FIG. 6.
Figure 8:
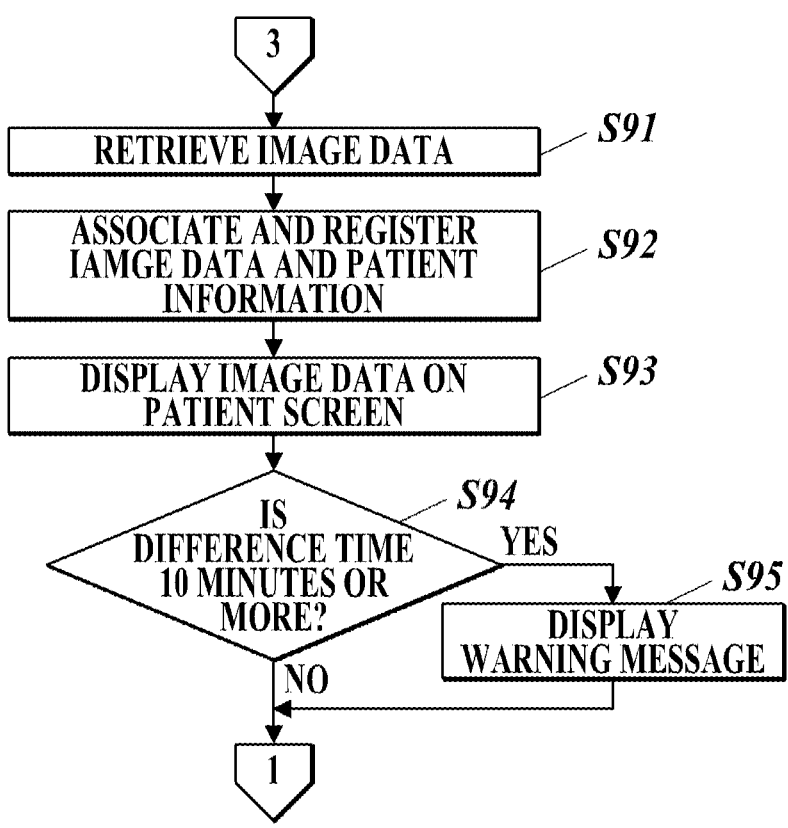
FIG. 8 is a flowchart showing the patient image associating processing following FIG. 6.
Figure 9:
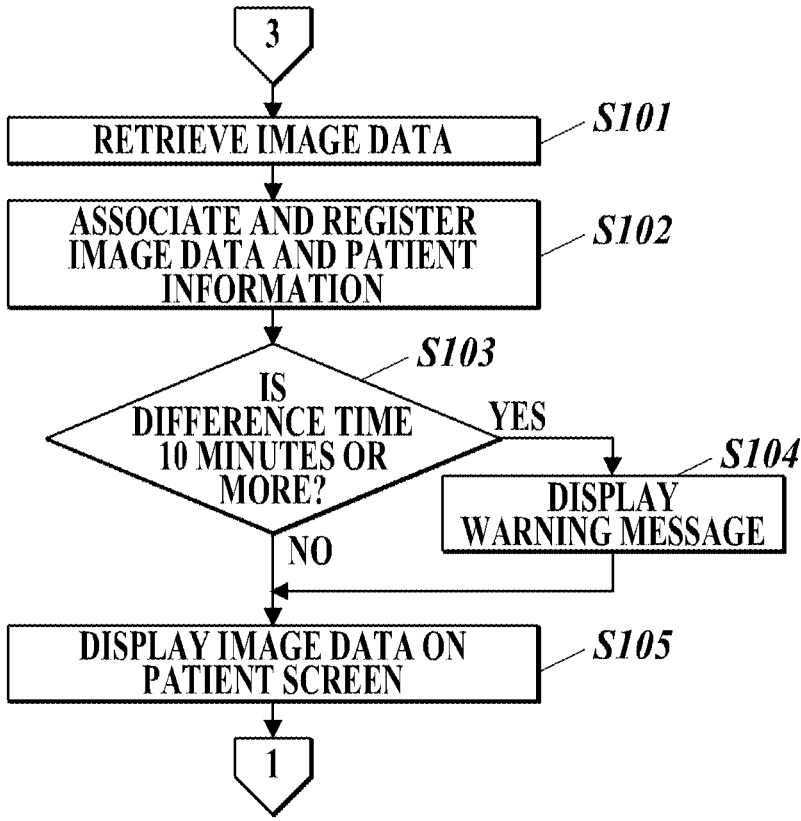
FIG. 9 is a flowchart showing image data retrieving processing in a first modification example.
Figure 10:
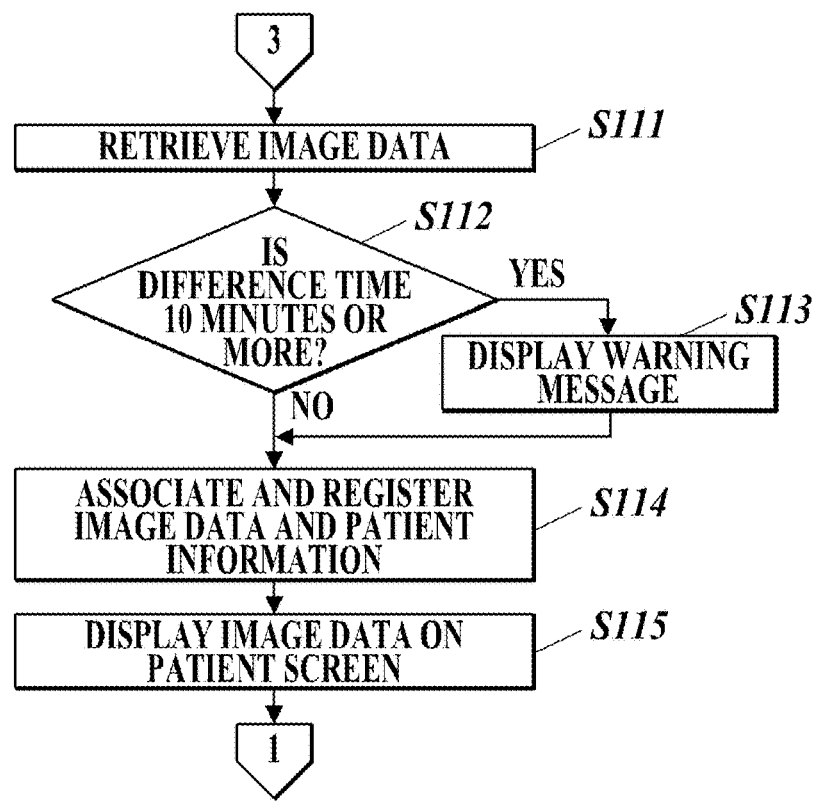
FIG. 10 is a flowchart showing image data retrieving processing in a second modification example.
Figure 11:
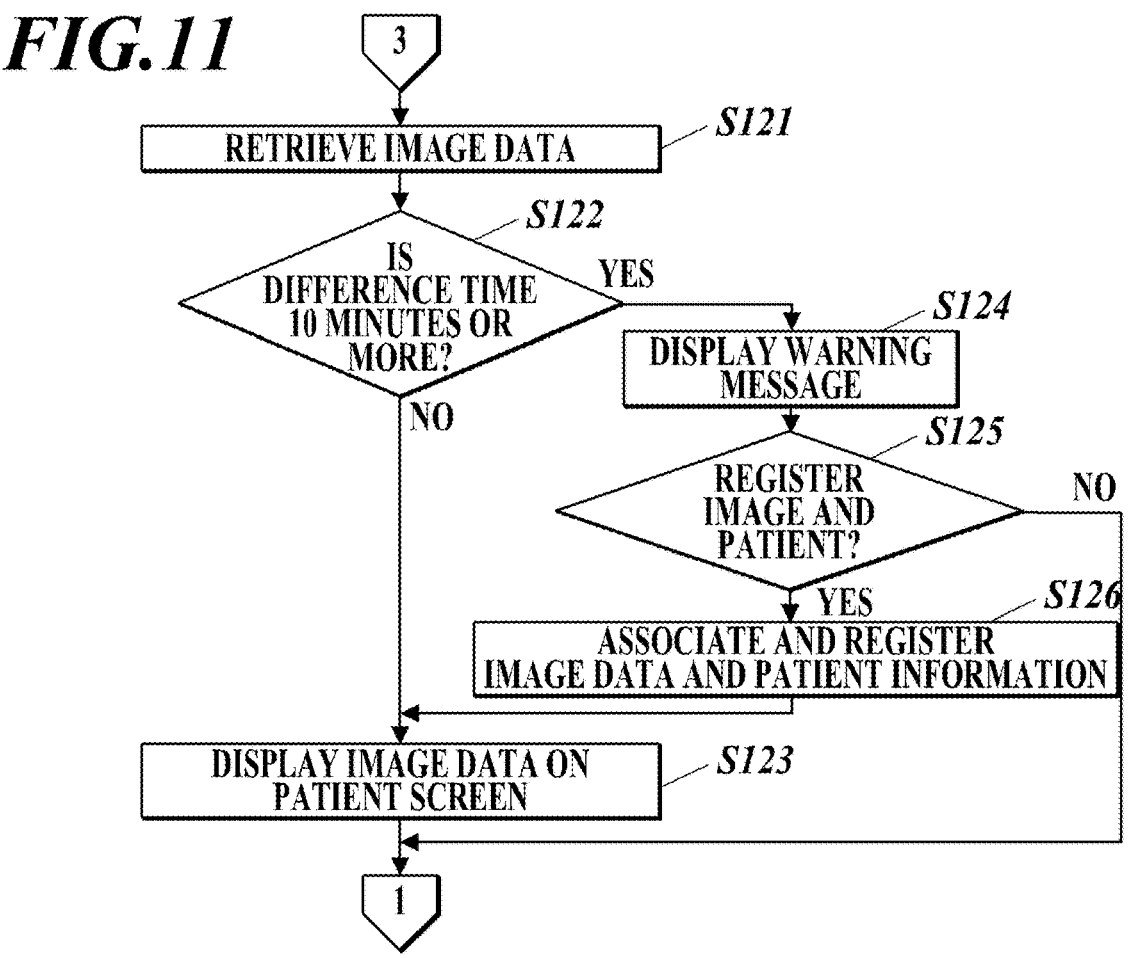
FIG. 11 is a flowchart showing image data retrieving processing in a third modification example.

The operation of the medical image management system 1 will be described with reference to FIG. 3 to FIG. 14. FIG. 3 is a flowchart showing patient retrieving mode setting processing. FIG. 4 is a flowchart showing imaging mode switching processing. FIG. 5 is a flowchart showing normal imaging processing. FIG. 6 is a flowchart showing patient image associating processing. FIG. 7 is a flowchart showing the patient image associating processing following FIG. 6. FIG. 8 is a flowchart showing the patient image associating processing following FIG. 6. FIG. 9 is a flowchart showing image data retrieving processing in a first modification example. FIG. 10 is a flowchart showing image data retrieving processing in a second modification example. FIG. 11 is a flowchart showing image data retrieving processing in a third modification example. FIG. 12 is a view showing a reception screen 100. FIG. 13 is a view showing a patient screen 300. FIG. 14 is a view showing a patient image associating screen 200.

In the present embodiment, in a medical image management system 1, there is performed patient image associating processing of performing memory imaging of DR imaging, retrieving image data of radiation image which was generated and stored in the FPD 25, and associating the retrieved image data with the patient information.

In the medical image management apparatus 3, patient retrieving mode setting processing is performed in advance. The patient retrieving mode includes a patient specified retrieving mode and a patient unspecified retrieving mode. The patient specified retrieving mode is a mode of retrieving the image data stored in the FPD 25 and associating the image data with the patient information of the patient that is currently displayed (specified) (for specifying the patient information of patient and retrieving the image data) when the patient screen indicating the patient information of the single patient is displayed in after-mentioned patient image associating processing. The patient unspecified retrieving mode is a mode of disabling the retrieving of the image data stored in the FPD 25 and the associating of the image data with the patient information of the patient that is currently displayed (for retrieving the image data without specifying the patient information of the patient) when the patient screen is displayed. In the patient retrieving mode setting processing, before the patient image associating processing, there is performed setting registration of the patient specified retrieving mode or the patient unspecified retrieving mode.

In the medical image management apparatus 3, for example, in response to a trigger that the instruction to execute the patient retrieving mode setting processing was input by the operator via the operating section 32, the controller 31 executes the patient retrieving mode setting processing in accordance with the patient retrieving mode setting program stored in the storage 33.

As shown in FIG. 3, the controller 31 first generates the patient retrieving mode setting screen for selecting and inputting the patient specified retrieving mode or the patient unspecified retrieving mode and causes the display section 34 to display the patient retrieving mode setting screen (step S1). The controller 31 receives the selection input of the patient specified retrieving mode or the patient unspecified retrieving mode from the operator via the operating section 32 (step S2).

The controller 31 stores and registers the setting information of the patient specified retrieving mode or the patient unspecified retrieving mode which was selected and input in step S2 (step S3), and ends the patient retrieving mode setting processing.

In the medical image management apparatus 3, remaining image patient specified retrieving setting processing is performed in advance. In the remaining image patient specified retrieving setting processing, when a single piece of image data of radiation image is stored in the FPD 25, there is performed setting to enable/disable the retrieving of the image data stored in the FPD 25 and associating of the image data with the patient information of the patient that is currently displayed.

With reference to FIG. 4, imaging mode switching processing executed by the FPD 25 will be described. The imaging mode switching processing is, for example, processing that is repeatedly executed at a predetermined cycle, and switching the imaging mode according to the operation input by the operator. In the FPD 25, for example, in response to a trigger that a predetermined time has passed, the controller 251 executes the imaging mode switching processing in accordance with the imaging mode switching program stored in the storage 253.

The controller 251 determines whether the imaging mode switching button of the operating section 252 was pressed and input by the operator (step S21). If the imaging mode switching button was not pressed and input (step S21; NO), the controller 251 ends the imaging mode switching processing. If the imaging mode switching button was pressed and input (step S21; YES), the controller 251 determines whether the pressing input of the imaging mode switching button in step S21 was the on input to switch to the memory imaging mode (step S22).

If the pressing input of the imaging mode switching button was the on input to the normal imaging mode (step S22; NO), the controller 251 performs on setting to the normal imaging mode (step S23). The controller 251 then performs setting to enable the network connection to the communication network 5 via the communicating section 255 (step S24), and ends the imaging mode switching processing.

If the pressing input of the imaging mode switching button was the on input to the memory imaging mode (step S22; YES), the controller 251 performs on setting to the memory imaging mode (step S25). The controller 251 performs setting to disable the network connection to the communication network via the communicating section 255 (step S26), and ends the imaging mode switching processing.

With reference to FIG. 5, normal imaging processing as the normal imaging of DR imaging executed by the medical image management apparatus 3 will be described. In the medical image management apparatus 3, for example, in response to a trigger that the instruction to execute the normal imaging processing was input by the operator such as a doctor and a technologist via the operating section 32, the controller 31 executes the normal imaging processing in accordance with the normal imaging program stored in the storage 33.

In the radiation imaging room of the medical facility, in advance, the patient of the DR imaging target is placed on the imaging table of the DR imaging device and the FPD 25 is set on the DR imaging device in a state in which the FPD 25 and the medical image management apparatus 3 can wirelessly communicate with each other via the access point of the communication network 5. The FPD 25 is set to switch to the normal imaging mode by the operation input of the switching switch by the operator. In the medical image management apparatus 3, all pieces of patient information for the DR imaging or the like are received from the reception apparatus 4 or generated in response to the input by the operator via the operating section 32, and stored in the storage 33.

The controller 31 first receives a click input of the patient reception button by the operator via the operating section 32 (step S31). The controller 31 then receives and registers the selection input of the patient information of the patient of DR imaging in the patient information stored in the storage 33 from the operator via the operating section 32 (step S32).

The controller 31 receives a click input of the consultation start button by the operator via the operating section 32 (step S33). The controller 31 causes the display section 34 to display the patient screen for displaying the image data of radiation image of the DR imaging (step S34). The patient screen includes an imaging preparation button for proceeding to the image data retrieving state of DR imaging.

The controller 31 receives a click input of the imaging preparation button from the operator via the operating section 32 (step S35).

The controller 31 receives the DR imaging operation input from the operator via the operating section 32, and transmits the operation information to the DR imaging device via the communicating section 36 to perform DR imaging (step S36). The controller 251 of the FPD 25 automatically detects the X-ray which was emitted for exposure from the DR imaging device, generates the image data of a single radiation image, temporarily saves, in the storage 253, the generated image data with accompanying information such as the imaging date and time of the image data based on the current date and time information output from the time counting section 256, and reads out the image data and the accompanying information. The controller 251 transmits the single piece of image data and the accompanying information which were saved to the medical image management apparatus 3 via the communicating section 255. The controller 31 then receives the single piece of image data and the accompanying information from the FPD 25 via the communicating section 36, and stores and retrieves the image data and the accompanying information into the storage 33 (step S37).

The controller 31 associates the image data (and accompanying information) received in step S37 from the operator via the operating section 32 with the patient information selected in step S32 (step S38). The controller 31 displays the image data (and accompanying information) and the patient information which were associated with each other in step S38 in the patient screen (step S39), and ends the normal imaging processing. The processing of steps S36 to S39 is repeated by the number of pieces of the image data captured.

With reference to FIG. 6 to FIG. 8, the patient image associating processing executed by the medical image management apparatus 3 will be described. The patient image associating processing is the processing of associating, with the patient information, at least one piece of image data stored in the FPD 25 by the memory imaging of DR imaging. In the patient image associating processing, it is also assumed that the FPD 25 in which a single piece of image data captured in the normal imaging is stored and not associated with the patient information is connected to the medical image management apparatus 3 when the power is turned off and turned on again or when the communication connection to the medical image management apparatus 3 is interrupted.

In advance, the operator as a person who performs imaging such as a doctor and a technologist goes to the hospital room where the (hospitalized) patient of the imaging target is located, with the FPD 25 and the X-ray device for doctor's rounds for check (not shown in the drawings). The FPD 25 is set to switch to the memory imaging mode enabling storing image data of a plurality of radiation images by the operation input of the imaging mode switching button by the operator. The operator performs the memory imaging as the DR imaging for at least one radiation image of each patient for at least one patient in the hospital room. The operator directs the radiation source of the X-ray device for doctor's rounds for check toward the patient of the imaging target, and arranges the FPD 25 such that the patient is located between the radiation source and the FPD 25. The operator performs operation input to the operating section of the console of the X-ray device for doctor's rounds for check and emits the X-ray for exposure from the radiation source at least once. The controller 251 of the FPD 25 automatically detects the X-ray emitted for exposure from the radiation source of the X-ray device for doctor's rounds for check to generate image data of at least one radiation image, and stores the image data with accompanying information such as the imaging date and time based on the current date and time information from the time counting section 256 in the storage 253. These processes are repeated by the amount of all the patients (all pieces of order information) of the imaging target. The operator makes a note of the captured patient(s), the number of captured image(s), and the captured portion(s). In the memory imaging, a lead marker of various types of characters may be used for the subject such that the lead marker is included in the image data. After the imaging, the operator presses and inputs the imaging mode switching button of the operating section 252 to set the FPD 25 to the normal imaging mode, and sets to enable the communication connection to the communication network 5.

In the medical image management apparatus 3, in response to a trigger that the instruction to execute the patient image associating processing was input by the operator via the operating section 32, the controller 31 executes the patient image associating processing in accordance with the patient image associating program stored in the storage 33.

As shown in FIG. 6, the controller 31 receives the communication connection of the FPD 25 which performed the memory imaging or the normal imaging via the communication network 5 (step S51). The controller 31 determines whether there is the image data of radiation image (remaining image data) stored in the connected FPD 25 (step S52). If the remaining image data does not exist (step S52; NO), the controller 31 ends the patient image associating processing.

If the remaining image data exists (step S52; YES), the controller 31 determines whether the imaging preparation button on the display screen of the display section 34 is turned on by a click input (step S53). As the display screen, for example, a reception screen 100 shown in FIG. 12, a patient screen 300 shown in FIG. 13, or the like is displayed. The reception screen 100 includes a patient information display region 110, a patient list 120, and a remaining image existing icon 130. The patient information display region 110 is a display region for displaying the patient information of the patient that is selected and input into a specified state (candidate of associating). The patient information display region 110 includes, for example, items such as the reception number of the patient, the patient ID, the photograph image, the patient name (kanji, kana, ASCII), the sex, the birth date, the age, the patient status icon, modality information, the reception time, today's comments, insurance information, urgency, and the patient memo.

The patient list 120 is a list of patient information for all the patients stored in the storage 33, and includes a search function of the patient information of the patient satisfying the search condition with the search condition input by the operator. The patient information which was selected and input by the operator in the patient list 120 is displayed in the patient information display region 110. It is possible to change whether or not to display the items displayed in the patient information display region 110 and the patient list 120 by setting. The remaining image existing icon 130 is an icon indicating that the remaining image data exists. The remaining image existing icon 130 is not displayed at the time of step S52.

As shown in FIG. 13, the patient screen 300 includes a patient display field 71 for displaying the patient ID and the patient name of the imaging target so as to enable visually confirming the patient for which the patient screen 300 is currently displayed. When the reception screen button 72 is operated, it is possible to return to the reception screen 100.

The patient screen 300 includes an image display field 73 for displaying the captured image, and a thumbnail display field 74 for displaying a thumbnail image. The patient screen 300 includes image data selection buttons 75 for selecting the image data for the present patient. By selecting desired image data with these image data selection buttons 75, it is possible to display the image in the image display field 73 and the thumbnail display field 74. For the image data selection buttons 75, it is possible to switch, with a display classification switching button 76, which of the classification is used for the arrangement, between the classification by the date and the classification by the type of the image generation apparatus (modality) 2.

The patient screen 300 includes a test suspending button 77 for inputting that the test is suspended for the image of the present patient, and a test end button 78 for inputting end of the test.

The patient screen 300 includes imaging preparation buttons 81 to retrieve image data from an external device. The imaging preparation button 81 is a button for retrieving image data from each type of devices of the image generation apparatus 2 connected to the communication network 5. In the present embodiment, five types of "CR", "US", "ES", "ECG" and "DR" of imaging preparation buttons 81 are arranged on the patient screen 300 to correspond to the types (ultrasonography (US) device 2*a*, endoscope (ES) 2*b*, electrocardiogram (ECG) device 2*c*, CR reading device 2*d*, and DR reading device 2*e*) of the image generation apparatus 2 connected to the communication network 5. Particularly, the imaging preparation button 81 for DR is an imaging preparation button 81*a*. When the imaging preparation button 81*a* is input, the image data is retrieved from the FPD 25.

The patient screen 300 includes image output buttons 82 for outputting the retrieved image data by printing, email transmission or the like, display switching buttons 83 for switching the display such as layout of image display field, and a remaining image existing icon 84 indicating that the remaining image data exists.

If the imaging preparation button is off (reception screen 100 is displayed, or patient screen 300 is displayed and imaging preparation button 81*a* is off) (step S53; NO), the controller 31 causes the display section 34 to display the remaining image existing icon indicating that the remaining image data exists (remaining image existing icon 130 in the reception screen 100, the remaining image existing icon 84 in the patient screen 300) (step S54).

The controller 31 receives a click input of the remaining image existing icon by the operator via the operating section 32 (step S55). The controller 31 determines whether the patient screen (for example, patient screen 300) indicating the patient information of the patient that is the association target is currently displayed (step S56).

If the patient screen is not currently displayed (step S56; NO), the controller 31 causes the display section 34 to display a retrieving checking message window (step S57). The retrieving checking message window includes for example, the message of "Retrieve untransferred image data in FPD? After retrieving, associate patient information with image data in patient image associating screen", "Yes" button for receiving the input to execute the image data retrieving, and "No" button for receiving the input not to execute the image data retrieving. If the patient screen is currently displayed (step S56; YES), the controller 31 refers to setting information of the patient specified retrieving mode/patient unspecified retrieving mode stored in the storage 33, and determines whether the current mode is the patient specified retrieving mode (step S58).

If the current mode is the patient unspecified retrieving mode (step S58; NO), when the controller 31 receives a click input of the imaging preparation button by the operator via the operating section 32 (step S59), the controller 31 displays a retrieving disabled message (window) indicating that the patient specified retrieving of image data is disabled (step S60). The retrieving disabled message window include, for example, the message of "You cannot retrieve image data in association with patient information. Close patient screen."

The controller 31 then closes the patient screen which is currently displayed (step S61), and proceeds to step S57. If the current mode is the patient specified retrieving mode (step S58; YES), the controller 31 retrieves the image data and the accompanying information from the FPD 25 which is currently connected via the communicating section 36 (step S62). In step S62, until the retrieving is completed, the controller 31 determines whether the retrieving of image data and accompanying information has been completed by determining whether the remaining image data which is not retrieved is left in the FPD 25. The same applies to steps S71 and S91.

The controller 31 generates a checking message (window) of registration of associating between a retrieved single piece of image data with the patient information of the patient screen currently displayed, and causes the display section 34 to display the checking message (window) (step S63). The checking message window includes, for example, a message of "Image data of past imaging was retrieved. Register the image data as image data of this patient?", "Yes" button for receiving the input to register the association between the retrieved image data and the patient information of the patient screen, and "No" button for receiving the input not to register the association.

The controller 31 determines whether registration of the association between the image data retrieved in step S62 and the patient information of the image which is currently displayed was input by the operator via the operating section 32 (whether click input was made to "Yes" button) (step S64). If the registration of association between the image data and the patient information was input (step S64; YES), the controller 31 associates the image data retrieved in step S62 and its accompanying information with the patient information of the patient that is currently displayed, and stores and registers the information in the storage 33 (step S65).

The controller 31 causes the display section 34 to display the image data (and its accompanying information), which was associated in step S65, in association with the patient information on the patient screen which is currently displayed (step S66), and ends the patient image associating processing. If the input not to register the association between the image data and the patient information was made (click input of "No" button was made) (step S64; NO), the controller 31 ends the patient image associating processing.

After step S57, the controller 31 determines whether to retrieve the image data from the currently-connected FPD 25 by the click input made to the "Yes" button from the operator via the operating section 32, or not to retrieve image data from the currently-connected FPD 25 by the click input made to the "No" button (step S67). If the image data is not to be retrieved (step S67; NO), the controller 31 ends the patient image associating processing.

If the image data is to be retrieved (step S67; YES), as shown in FIG. 7, the controller 31 retrieves the image data and its accompanying information from the FPD 25 which is currently connected via the communicating section 36 (step S71). The controller 31 generates the patient image associating screen and causes the display section 34 to display the patient image associating screen (step S72). The patient image associating screen is, for example, the patient image associating screen 200 shown in FIG. 14. The patient image associating screen 200 includes an image list 210 and a patient list 220. The image list 210 is a display region to display as a list, for each image, accompanying information of items such as the thumbnail image of the retrieved image data, the type of image generator (modality) (DR in the present embodiment) which captured the image of the image data that was retrieved, and the imaging date and time of the image data (exposure date and time). The items included in the image list 210 may include items such as the patient ID, the patient name (kanji, kana, and ASCII), the sex of the patient, the birth date, unconfirmed matters, and FPD identification information. As for each item displayed in the image list 210, it is possible to change whether to display or not to display the item by setting.

The patient list 220 is display information similar to the patient list 120. The return button 230 is a button for receiving the input by the operator to close the patient image associating screen 200 and return to the display screen displayed at the previous stage.

According to the input of search conditions made by the operator in the patient list (patient list 220) of the patient image associating screen via the operating section 32, the controller 31 searches for the patient information of the patients satisfying the search conditions in the patient information stored in the storage 33, and displays the patient information of the search results in the patient list (step S73). The controller 31 receives the selection input of image data from the image list (image list 210) of the patient image associating screen and the selection input of the patient information from the patient list and receives the click input of the return button (return button 230) (step S74).

The controller 31 generates the confirmation checking message (window) and causes the display section 34 to display the generated message, and determines whether the input to confirm the association between the image data and the patient information selected in step S74 was made by the operator via the operating section 32 (step S75). The confirmation checking message window includes, for example, the message of "Associate patient with image data?", "Yes" button for receiving the input to confirm the association, and "No" button for receiving the input not to confirm the association. If the input to confirm the association between the image data and the patient information (click input of "Yes" button) was made (step S75; YES), the controller 31 associates the image data selected in step S74 (and its accompanying information) with the selected patient information, and stores and registers them in the storage 33 (step S76).

The controller 31 then closes the patient image associating screen (step S77), and ends the patient image associating processing. If the input to confirm the association between the image data and the patient information was not made (click input of "No" button was made) (step S75; NO), the controller 31 proceeds to step S77.

Returning to FIG. 6, if the imaging preparation button is turned on by the click input (the patient screen 300 is displayed and the imaging preparation button 81a is turned on) (step S53; YES), as shown in FIG. 8, the controller 31 retrieves the image data and its accompanying information from the FPD 25 which is currently connected via the communicating section 36 (step S91). The controller 31 associates the image data and its accompanying information retrieved in step S91 with the patient information of the patient image which is currently displayed, and stores and registers them in the storage 33 (step S92).

The controller 31 displays the image data (and its accompanying information) associated in step S92 in association with the patient information on the patient screen which is currently displayed (step S93). The controller 31 then obtains the current date and time information from the time counting section 37, calculates a difference time between the imaging date and time of the accompanying information of the image data associated in step S92 and the obtained current date and time information, and determines whether or not the difference time is 10 minutes as a predetermined time or more (step S94). This predetermined time of 10 minutes is an example, and the predetermined time is not limited to 10 minutes.

If the difference time is less than 10 minutes (step S94; NO), the controller 31 determines that the retrieved image data is in the state corresponding to the normal imaging (temporary interruption of communication), and ends the patient image associating processing. If the difference time is 10 minutes or more (step S94; YES), the controller 31 determines that the retrieved image data is in the state corresponding to the memory imaging, generates a warning message (window) and causes the display section 34 to display the message (step S95), and ends the patient image associating processing. The warning message window includes, for example, the message of "Retrieved image data is image data of image captured in the past. Make sure retrieved image data is image data of this patient."

With reference to FIG. 9, a first modification example of processing of steps S91 to S95 in FIG. 8 (referred to as image data retrieving processing) will be described. As shown in FIG. 9, the steps S101 to S105 of the image data retrieving processing in the first modification example are similar to the steps S91, S92, S94, S95 and S93 in FIG. 8.

With reference to FIG. 10, a second modification example of the image data retrieving processing of steps S91 to S95 in FIG. 8 will be described. As shown in FIG. 10, the steps S111 to S115 of the image data retrieving processing in the second modification example are similar to the steps S91, S94, S95, S92 and S93 in FIG. 8.

With reference to FIG. 11, a third modification example of the image data retrieving processing of steps S91 to S95 in FIG. 8 will be described. As shown in FIG. 11, the steps S121 to S123 and S126 of the image data retrieving processing in the third modification example are similar to the steps S91, S94, S93 and S92 in FIG. 8.

If the difference time is 10 minutes or more (step S122; YES), the controller 31 generates a warning message (window) of registration of association between the retrieved image data and the patient information of the patient screen which is currently displayed, and causes the display section 34 to display the message (step S124). The warning message window includes, for example, the message of "Retrieved image data is image data of image captured in the past. Register image data as image data of this patient?", the "Yes" button for receiving the input to register the association between the retrieved image data and the patient information of the patient screen, and the "No" button for receiving the input not to register the association. The controller 31 determines whether the input to register the association between the image data retrieved in step S121 and the patient information of the patient screen which is currently displayed (click input of "Yes" button) was made by the operator via the operating section 32 (step S125).

If the input to register the association was made (step S125; YES), the controller 31 executes step S126, and proceeds to step S123. If the input not to register the association (click input of "No" button) was made (step S125; NO), the controller 31 ends the patient image associating processing. That is, if the difference time is 10 minutes or more (step S122; YES), the controller 31 determines that the imaging is the memory imaging, and disables the automatic associating between the image data and the patient information in step S126.

In the image data retrieving processing in FIG. 8 to FIG. 11, the steps of determining the difference time and displaying the warning message (window) may be performed before the step of image data retrieving (or associating between image data and patient information), that is, before the step of retrieving the image data or the step of associating the image data with the patient information.

In the steps S94, S103, S112 and S122 of the image data retrieving processing of FIG. 8 to FIG. 11, whether or not the time difference between the imaging date and time (imaging time) and the image data retrieving date and time (retrieving time, current date and time) is a predetermined time or more is determined. However, the present invention is not limited to this. For example, in steps S94, S103, S112 and S122, the controller 31 may determine whether or not at least one of time differences is the predetermined time or more, the time differences being the time difference between the imaging time and the retrieving time of the retrieved image data, the time difference between the patient specifying time when the patient was specified and the imaging time or the retrieving time, the time difference between the disconnecting time when the FPD 25 disconnected the communication and the retrieving time or the imaging time, and the time difference between the previous imaging time which is imaging time of an image captured before imaging of the image data and the present imaging time of the image data which was retrieved this time. Alternatively, whether or not the operation time of operating the imaging preparation button or selection of the patient information is after the imaging time may be determined. If the determination result of any of the above determinations is yes, the imaging is determined as the memory imaging. If the determination result is no, the imaging is determined as the normal imaging.

As described above, according to the present embodiment, the medical image management apparatus 3 includes a controller 31 that retrieves, via a communicating section 36, image data from the FPD 25 which generates and stores the image data of the medical image. In retrieving the image data obtained by memory imaging, the controller 31 disables automatic associating of the image data obtained by the memory imaging with the patient information, or disables retrieving of the image data obtained by the memory imaging in a state in which the image data obtained by the memory imaging is automatically associated with the patient information.

When the image data obtained by the memory imaging is retrieved, and when the current mode is set to the memory imaging mode, the controller 31 may disable retrieving the image data from the FPD 25 into the medical image management apparatus 3 in a state in which the patient information is specified. In more detail, in a state in which the image data is to be retrieved into the medical image management apparatus 3 without specifying the patient information of the patient (for example, when the current mode is set to the patient unspecified retrieving mode), the controller 31 basically does not disable retrieving of the image data from the FPD 25 into the medical image management apparatus 3. However, even in a state in which the image data is to be retrieved into the medical image management apparatus without specifying the patient information of the patient (for example, patient unspecified retrieving mode), in the setting in which the patient information is specified and the image data is to be automatically associated with the patient information which is currently specified, the controller 31 disables retrieving of the image data from the FPD 25 into the medical image management apparatus 3.

Thus, it is possible to prevent the retrieved image data from being automatically associated with the patient information which is currently specified, and prevent the image data from being associated with wrong patient information. Accordingly, it is possible to prevent a plurality of pieces of image data generated by the memory imaging from being associated with wrong one piece of patient information.

When the current mode is set to the patient unspecified retrieving mode and on input is made to the imaging preparation button which receives the input for retrieving the image data, the controller 31 causes the display 34 to display the warning information indicating disabling of retrieving the image data from the FPD 25 so as to be associated with the patient information which is currently specified. Thus, it is possible to visually confirm that the retrieving of image data in association with wrong patient information is disabled.

The controller 31 retrieves the image data from the FPD 25 after the warning information is displayed, and the controller 31 causes the display 34 to display the patient image associating screen for associating the retrieved image data with the patient information in response to the completion of retrieving. Thus, by automatically displaying the patient image associating screen, it is possible to reduce the work burden of associating the image data with the patient information, prevent the forgetting of associating, and surely execute the associating by the patient image associating screen.

The controller 31 receives, via the operating section 32, the selection input and sets the inputted selection, the selection input selecting a patient unspecified retrieving mode or a patient specified retrieving mode for retrieving the image data from the FPD 25 so as to be associated with the patient information which is currently specified. Thus, it is possible to freely set the patient unspecified retrieving mode and the patient specified retrieving mode.

The description in the above embodiment is a preferred example of a medical image management apparatus, a medical image management method and a program according to the present invention, and the present invention is not limited to this.

Figure 15:
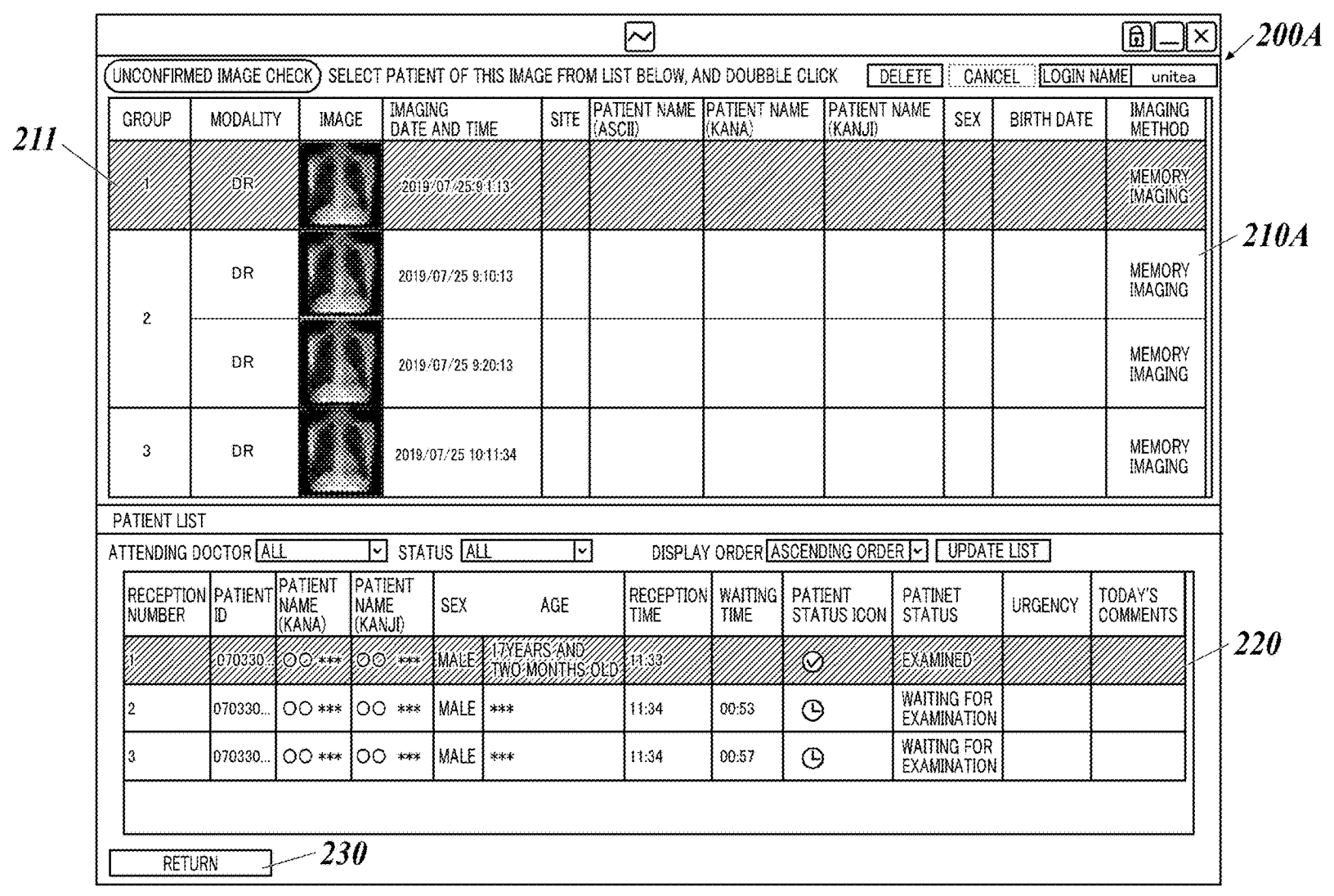
Figure 16:
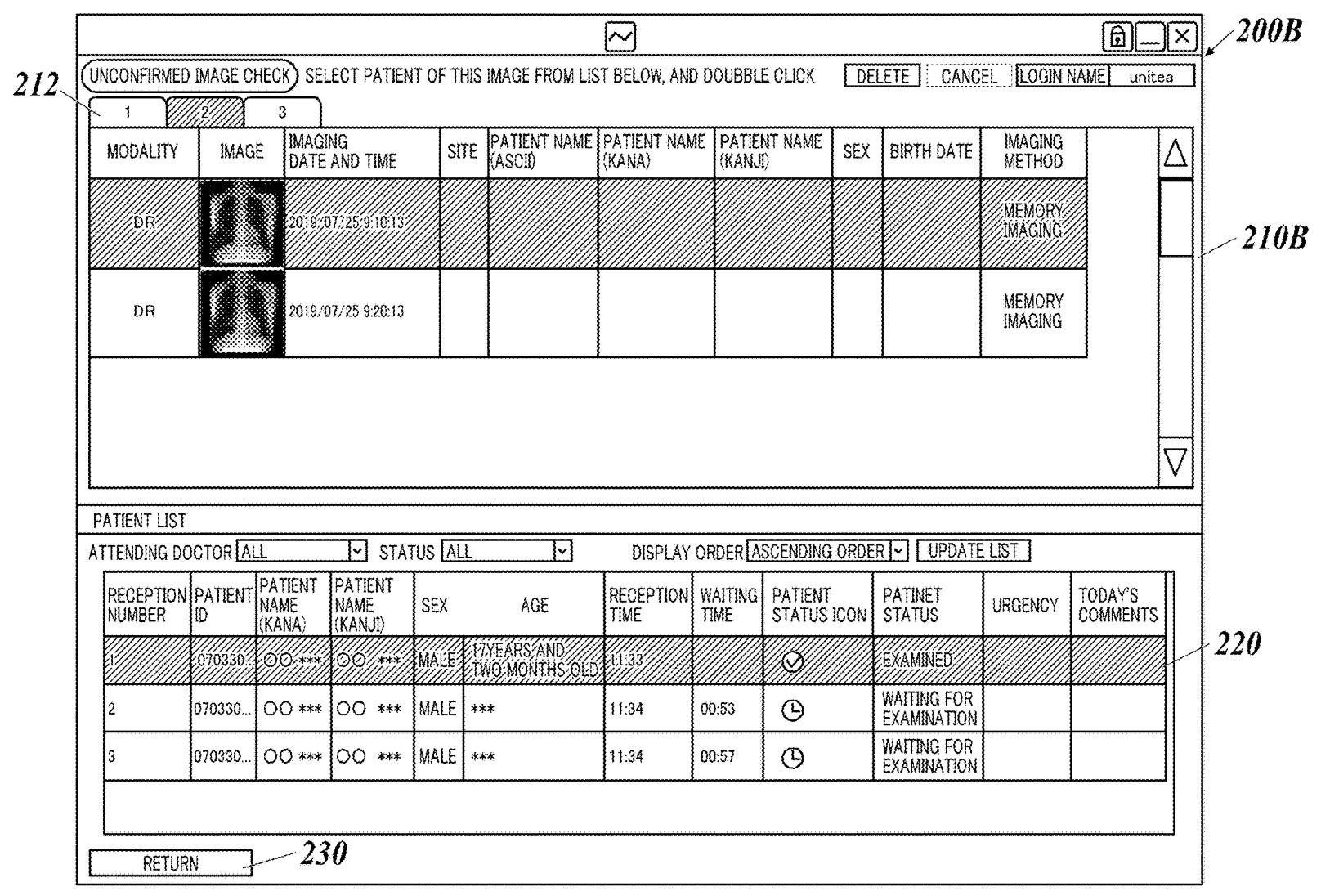
Figure 18:
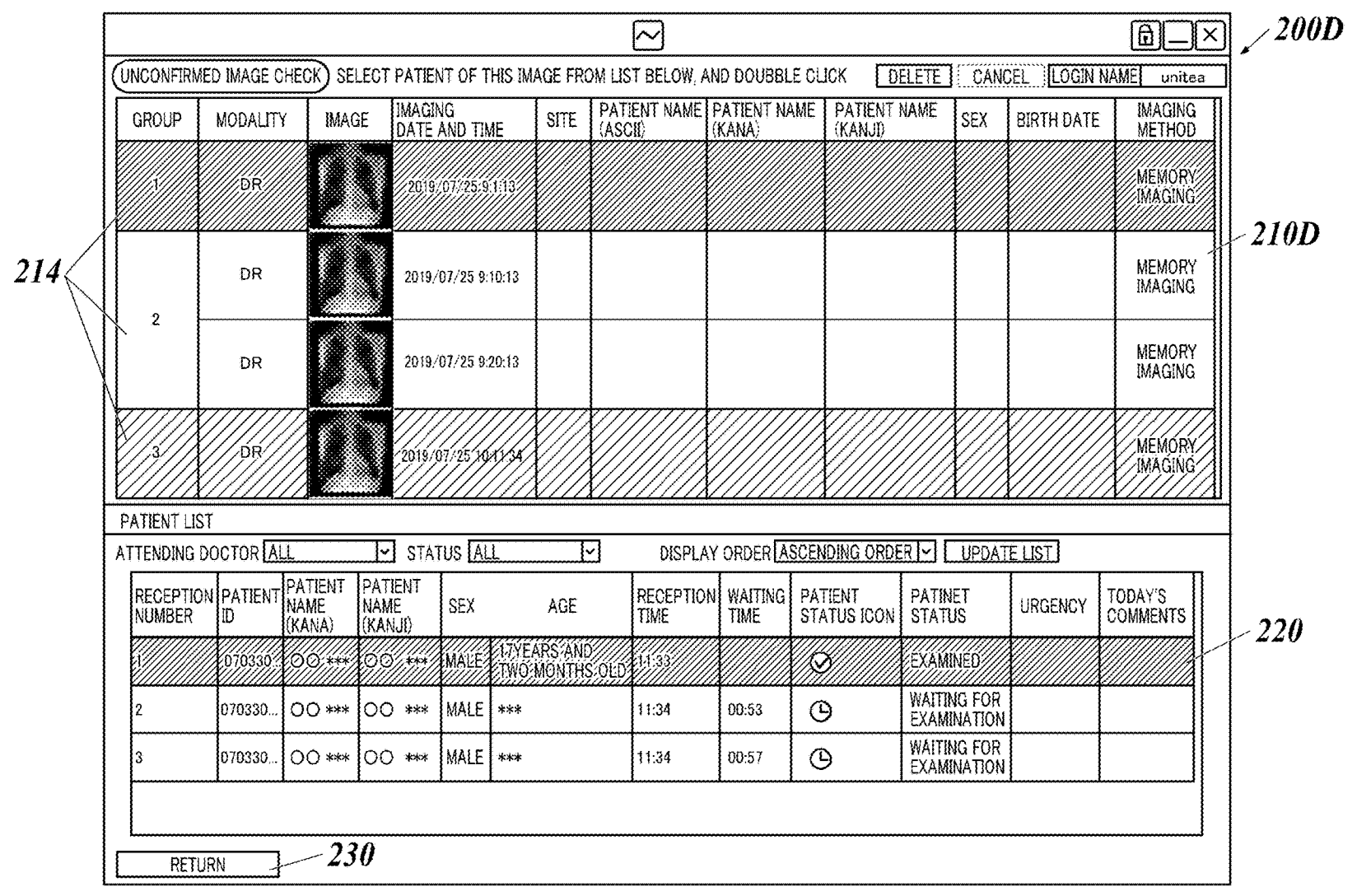
Figure 19:
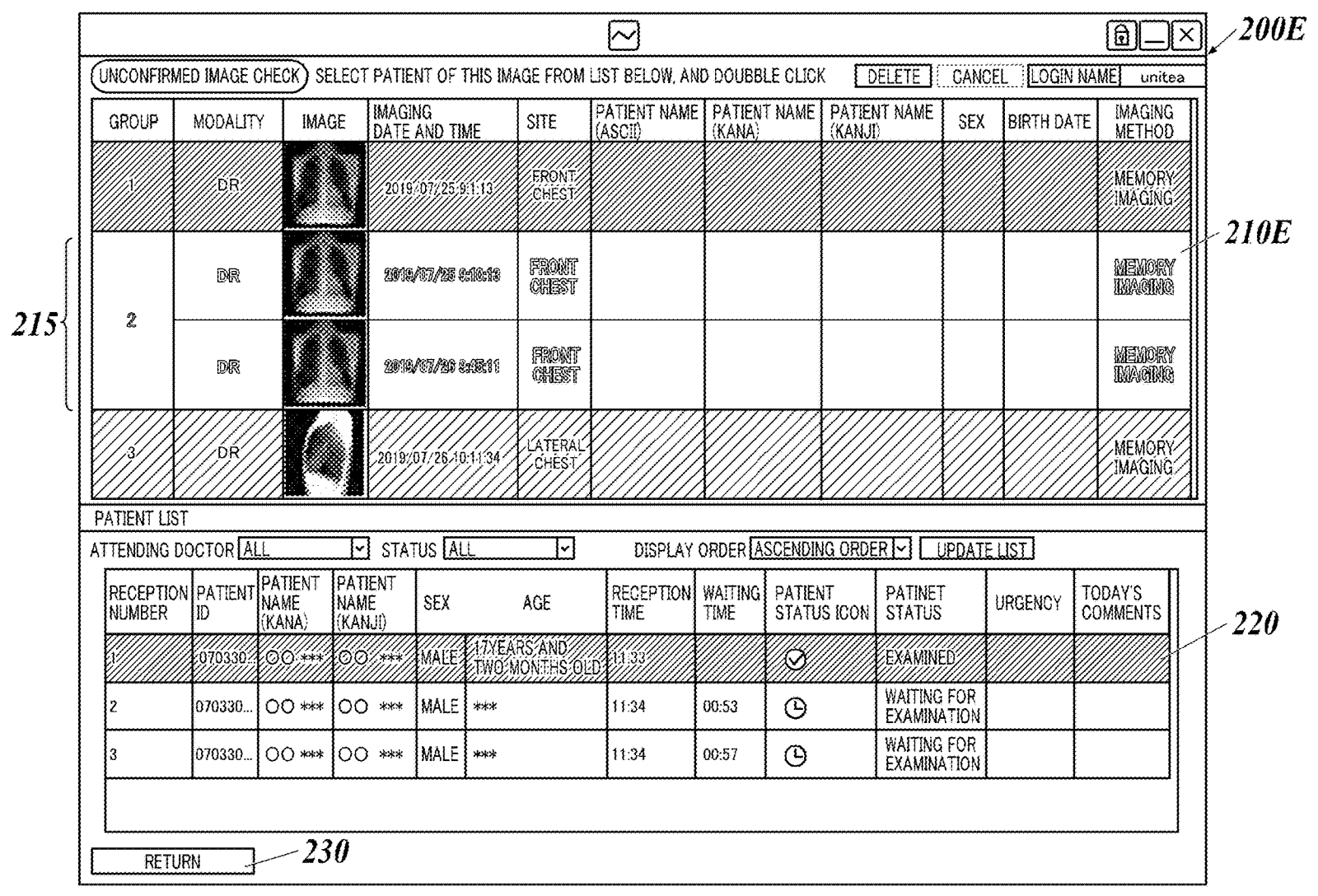

For example, in the above embodiment, the image of image data and the information regarding the image are simply displayed as a list in the image list 210 of the patient image associating screen 200 shown in FIG. 14. However, the present invention is not limited to this. FIG. 15 is a view showing a patient image associating screen 200A. FIG. 16 is a view showing a patient image associating screen 200B. FIG. 17 is a view showing a patient image associating screen 200C. FIG. 18 is a view showing a patient image associating screen 200D. FIG. 19 is a view showing a patient image associating screen 200E.

In the memory imaging of FPD 25, the controller 251 of the FPD 25 can receive the input of dividing information for dividing a plurality of pieces of image data made by the operator via the operating section 252. Thus, the controller 251 of the FPD 25 receives the dividing information from a mobile terminal via the communicating section 255, stores the plurality of pieces of image data in the storage 253, and stores the accompanying information including the imaging date and time and the dividing information in the storage 253. In the step S71 of the patient image associating processing, for example, the image data and the accompanying information including the dividing information are read out from the FPD 25.

In step S72, the controller 31 may generate and display the patient image associating screen 200A shown in FIG. 15, instead of the patient image associating screen 200. The patient image associating screen 200A includes an image list 210A, a patient list 220 and a return button 230. In the image list 210A, grouping is performed to a plurality of pieces of retrieved image data and the accompanying information such as the type of modality corresponding to each piece of image data, according to the dividing information. The column of group 211, the column of image data of the group, and the column of the accompanying information of the image data are displayed as a list in a table form.

In step S72, the controller 31 may generate and display the patient image associating screen 200B shown in FIG. 16. The patient image associating screen 200B includes an image list 210B, a patient list 220 and a return button 230. In the image list 210B, grouping is performed to a plurality of pieces of retrieved image data and the accompanying information such as the type of modality corresponding to each piece of image data, according to the dividing information. The column of image data of a selected group and the column of the accompanying information of the image data are displayed as a list, according to the selection input of the tab 212 of each group.

In step S72, the controller 31 may generate and display the patient image associating screen 200C shown in FIG. 17. The patient image associating screen 200C includes an image list 210C, a patient list 220 and a return button 230. In the image list 210C, grouping is performed to a plurality of pieces of retrieved image data and the accompanying information such as the type of modality corresponding to each piece of image data, according to the dividing information. The column of image data of a selected group and the column of the accompanying information of the image data are displayed as a list, according to the selection input of the button 213 of each group.

In step S72, the controller 31 may generate and display the patient image associating screen 200D shown in FIG. 18. The patient image associating screen 200D includes an image list 210D, a patient list 220 and a return button 230. In the image list 210D, grouping is performed to a plurality of pieces of retrieved image data and the accompanying information such as the type of modality corresponding to each piece of image data, according to the dividing information. The column of each group, the column of image data of the group and the column of the accompanying information of the image data are color-coded by the color-code 214 for each group, and displayed as a list.

The present invention is not limited to the configuration of performing grouping according to the dividing information. The controller 31 may perform the grouping by using at least one of recognizing information by image recognition of a lead marker portion in the retrieved image data, the dividing information, the imaging date and time of the retrieved image data, and the order information.

In step S72, the controller 31 may generate and display the patient image associating screen 200E shown in FIG. 19. The patient image associating screen 200E includes an image list 210E, a patient list 220 and a return button 230. In the image list 210E, grouping is performed to a plurality of pieces of retrieved image data and the information such as the type of modality corresponding to each piece of image data, according to the dividing information. The column of each group, the column of image data of the group and the column of the accompanying information of the image data are displayed as a list. The accompanying information includes a(n) (imaging) site. In step S72, the controller 31 automatically recognizes the imaging site in the image data by image recognition such as pattern recognition and includes the recognized imaging site in the accompanying information of the image data. The imaging date and times of the two pieces of image data in the group 2 are different by a predetermined time or more, and the imaging sites are same. Thus, warning information 215 emphasizing by changing the color of the characters warns that there is a possibility of different patients even in the same group. The warning information 215 is not limited to the change of colors of the characters, and may be expressed by a warning message or other various types of expression forms.

In such a way, the controller 31 displays warning information for image data having a possibility of different patients, even in a same group. Whether to display or not to display the warning information may be set. For pieces of image data of a same group, the controller 31 determines at least one of (1) whether or not the imaging date and times of image data are different by a predetermined time or more, (2) combination of imaging sites, and (3) comparison of images of a same imaging site. By the determination result, the controller 31 determines whether the image data has a possibility of different patients.

As for (1), when the imaging date and times are largely different from each other by the predetermined time (for example, 10 minutes) or more, the controller 31 determines that there is a possibility that the patients are different. This predetermined time can be set to change by a setting input of the operator, for example. As for (2), when the imaging sites are different such that, for example, the imaging sites are chest and toe which are different from each other though the pieces of image data are in the same group, the controller 31 determines that there is a possibility of different patients. However, when the imaging sites are a combination which is likely to be captured at once for a same patient, the controller 31 determines that there is no possibility of different patients. The combination of imaging sites which is likely to be captured at once can be set to change by a setting input of the operator, for example. As for (3), when a plurality of pieces of image data have a same imaging site, the controller 31 compares the images and determines whether the patients are a same patient. The comparison for determining whether the patients are identical is performed by using the function of temporal difference. In a case of less than a threshold (for example, 95%) of percentage of image matching by the temporal difference, the controller 31 determines that there is a possibility of different patients. This threshold of percentage of image matching can be set to change by a setting input of the operator, for example.

In the above embodiment, the target to be associated with the image data retrieved from the FPD 25 is the patient information. However, the present invention is not limited to this. The target to be associated with the image data may be order information which is information regarding the imaging for each imaging, or may be patient information and order information. The order information may include at least part of the patient information, or may not include the patient information. That is, the target to be associated with the image data is at least one of the patient information and the order information. The unspecified retrieving mode is a mode of retrieving the image data without specifying any of the patient information and the order information.

The above embodiment has been described for a human patient as a subject of imaging. However, the present invention is not limited to this, The subject of imaging may be animals.

According to the above embodiment, it is possible to prevent image data from being associated with at least one of patient information and order information which is wrong.

As for the other detailed configurations and the detailed operations of devices forming the medical image management system 1 in the above embodiments, modifications can be made as needed within the scope of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:

1. A medical image management apparatus comprising a hardware processor that:
retrieves image data from an image capturer which is a Flat Panel Detector (FPD) that generates and stores the image data of a medical image; and
in retrieving the image data that is generated by imaging with an imaging method in which the image data is stored in the image capturer without associating at least one of patient information of a patient and order information with the image data, and stored in the image capturer,
disables automatic associating of the image data obtained by the imaging with the imaging method with at least one of the patient information and the order information or
disables retrieving of the image data obtained by the imaging with the imaging method in a state in which the image data obtained by the imaging with the imaging method is automatically associated with at least one of the patient information and the order information, in a state that a single piece of image data of radiation image is stored in the FPD, sets to enable/disable the retrieving of the image data stored in the FPD and associating of the image data with the patient information of the patient that is currently displayed, in a state that an imaging mode switching button was pressed and input, determines whether the pressing input of the imaging mode switching button was an on input to switch to a memory imaging mode, in a state that the pressing input of the imaging mode switching button was the on input to a normal imaging mode, performs on setting to the normal imaging mode, and then performs setting to enable a network connection to a communication network, and ends an imaging mode switching processing, and in a state that the pressing input of the imaging mode switching button was the on input to the memory imaging mode, performs on setting to the memory imaging mode, and then performs setting to disable the network connection to the communication network, and ends the imaging mode switching processing.

2. The medical image management apparatus according to claim 1, wherein the hardware processor is set in advance to an unspecified retrieving mode for retrieving the image data without specifying the patient information of the patient or the order information of the imaging, and in response to an input of an image retrieving button that receives input for retrieving the image data, the hardware processor causes a display to display warning information indicating disabling of retrieving the image data from the image capturer so as to be associated with the at least one of the patient information and the order information that is currently specified.

3. The medical image management apparatus according to claim 2, wherein the hardware processor retrieves the image data from the image capturer after the warning information is displayed, and the hardware processor causes the display to display an image associating screen for associating the retrieved image data with the at least one of the patient information and the order information in response to completion of retrieving at least one piece of the image data.

4. The medical image management apparatus according to claim 1, wherein the hardware processor receives a selection input and sets inputted selection, the selection input selecting an unspecified retrieving mode for retrieving the image data without specifying the patient information of the patient or the order information of the imaging or a specified retrieving mode for retrieving the image data from the image capturer so as to be associated with at least one of the patient information and the order information that is currently displayed.

5. A medical image management apparatus comprising a hardware processor that:

retrieves image data from an image capturer which is a Flat Panel Detector (FPD) that generates and stores the image data of a medical image; and in a state in which the image data is to be retrieved without specifying patient information of a patient or order information of imaging, disables retrieving the image data, which is imaged with an imaging method in which the image data is stored in the image capturer without associating at least one of the patient information and the order information with the image data, from the image capturer so as to automatically associate the image data with at least one of the patient information and the order information that is currently specified, in a state that a single piece of image data of radiation image is stored in the FPD, sets to enable/disable the retrieving of the image data stored in the FPD and associating of the image data with the patient information of the patient that is currently displayed, in a state that an imaging mode switching button was pressed and input, determines whether the pressing input of the imaging mode switching button was an on input to switch to a memory imaging mode, in a state that the pressing input of the imaging mode switching button was the on input to a normal imaging mode, performs on setting to the normal imaging mode, and then performs setting to enable a network connection to a communication network, and ends an imaging mode switching processing, and in a state that the pressing input of the imaging mode switching button was the on input to the memory imaging mode, performs on setting to the memory imaging mode, and then performs setting to disable the network connection to the communication network, and ends the imaging mode switching processing.

6. The medical image management apparatus according to claim 5, wherein the hardware processor is set in advance to an unspecified retrieving mode for retrieving the image data without specifying the patient information of the patient or the order information of the imaging, and in response to an input of an image retrieving button that receives input for retrieving the image data, the hardware processor causes a display to display warning information indicating disabling of retrieving the image data from the image capturer so as to be associated with the at least one of the patient information and the order information that is currently specified.

7. The medical image management apparatus according to claim 6, wherein the hardware processor retrieves the image data from the image capturer after the warning information is displayed, and the hardware processor causes the display to display an image associating screen for associating the retrieved image data with the at least one of the patient information and the order information in response to completion of retrieving at least one piece of the image data.

8. The medical image management apparatus according to claim 5, wherein the hardware processor receives a selection input and sets inputted selection, the selection input selecting an unspecified retrieving mode for retrieving the image data without specifying the patient information of the patient or the order information of the imaging or a specified retrieving mode for retrieving the image data from the image capturer so as to be associated with at least one of the patient information and the order information that is currently displayed.

9. A medical image management method being performed by a hardware processor and comprising:

retrieving that is retrieving image data from an image capturer which is a Flat Panel Detector (FPD) that generates and stores the image data of a medical image; and controlling that is, in retrieving the image data which is generated by imaging with an imaging method in which the image data is stored in the image capturer without associating at least one of patient information of a patient and order information with the image data, and stored in the image capturer, disabling automatic associating of the image data obtained by the imaging with the imaging method with at least one of the patient information and the order information or disables retrieving of the image data obtained by the imaging with the imaging method in a state in which the image data obtained by the imaging with the imaging method is automatically associated with at least one of the patient information and the order information, in a state that a single piece of image data of radiation image is stored in the FPD, setting to enable/disable the retrieving of the image data stored in the FPD and associating of the image data with the patient information of the patient that is currently displayed, in a state that an imaging mode switching button was pressed and input, determining whether the pressing input of the imaging mode switching button was an on input to switch to a memory imaging mode, in a state that the pressing input of the imaging mode switching button was the on input to a normal imaging mode, performing on setting to the normal imaging mode, and then performing setting to enable a network connection to a communication network, and ends an imaging mode switching processing, and in a state that the pressing input of the imaging mode switching button was the on input to the memory imaging mode, performing on setting to the memory imaging mode, and then performing setting to disable the network connection to the communication network, and ending the imaging mode switching processing.

10. The medical image management method according to claim 9, wherein, in the controlling, the hardware processor is set in advance to an unspecified retrieving mode for retrieving the image data without specifying the patient information of the patient or the order information of imaging, and in response to an input of an image retrieving button that receives input for retrieving the image data, the hardware processor causes the display to display warning information, the warning information indicating disabling of retrieving the image data from the image capturer so as to be associated with the at least one of the patient information and the order information that is currently specified.

11. The medical image management method according to claim 10, wherein, in the controlling, after the warning information is displayed, the hardware processor retrieves the image data from the image capturer by the retrieving, and causes the display to display an image associating screen for associating the retrieved image data with the at least one of the patient information and the order information in response to completion of retrieving at least one piece of the image data.

12. The medical image management method according to claim 9, further comprising setting that is receiving a selection input and setting inputted selection, the selection input selecting an unspecified retrieving mode for retrieving the image data without specifying the patient information of the patient or the order information of the imaging or a specified retrieving mode for retrieving the image data from the image capturer so as to be associated with at least one of the patient information and the order information that is currently displayed.

13. A medical image management method being performed by a hardware processor and comprising:

retrieving that is retrieving image data from an image capturer which is a Flat Panel Detector (FPD) that generates and stores the image data of a medical image; and controlling that is, in a state in which the image data is to be retrieved without specifying patient information of a patient or order information of imaging, disabling retrieving the image data, which is imaged with an imaging method in which the image data is stored in the image capturer without associating at least one of the patient information and the order information with the image data, from the image capturer by the retrieving so as to automatically associate the image data with at least one of the patient information and the order information which is currently specified, in a state that a single piece of image data of radiation image is stored in the FPD, setting to enable/disable the retrieving of the image data stored in the FPD and associating of the image data with the patient information of the patient that is currently displayed, in a state that an imaging mode switching button was pressed and input, determining whether the pressing input of the imaging mode switching button was an on input to switch to a memory imaging mode, in a state that the pressing input of the imaging mode switching button was the on input to a normal imaging mode, performing on setting to the normal imaging mode, and then performing setting to enable a network connection to a communication network, and ends an imaging mode switching processing, and in a state that the pressing input of the imaging mode switching button was the on input to the memory imaging mode, performing on setting to the memory imaging mode, and then performing setting to disable the network connection to the communication network, and ending the imaging mode switching processing.

14. The medical image management method according to claim 13, wherein, in the controlling, the hardware processor is set in advance to an unspecified retrieving mode for retrieving the image data without specifying the patient information of a patient or the order information of the imaging, and in response to an input of an image retrieving button that receives input for retrieving the image data, the hardware processor causes the display to display warning information, the warning information indicating disabling of retrieving the image data from the image capturer so as to be associated with the at least one of the patient information and the order information that is currently specified.

15. The medical image management method according to claim 14, wherein, in the controlling, after the warning information is displayed, the hardware processor retrieves the image data from the image capturer by the retrieving, and causes the display to display an image associating screen for associating the retrieved image data with the at least one of the patient information and the order information in response to completion of retrieving at least one piece of the image data.

16. The medical image management method according to claim 13, further comprising setting that is receiving a selection input and setting inputted selection, the selection input selecting an unspecified retrieving mode for retrieving the image data without specifying the patient information of the patient or the order information of the imaging or a specified retrieving mode for retrieving the image data from the image capturer so as to be associated with at least one of the patient information and the order information that is currently displayed.

17. A non-transitory recording medium storing a computer readable program causing a computer to function as:
- a retriever that retrieves image data from an image capturer which is a Flat Panel Detector (FPD) that generates and stores the image data of a medical image; and
- a controller that, in retrieving the image data which is generated by imaging with an imaging method in which the image data is stored in the image capturer without associating at least one of patient information and order information with the image data, and stored in the image capturer,
- disables automatic associating of the image data obtained by the imaging with the imaging method with at least one of the patient information of a patient and the order information or
- disables retrieving of the image data obtained by the imaging with the imaging method in a state in which the image data obtained by the imaging with the imaging method is automatically associated with at least one of the patient information and the order information,
- in a state that a single piece of image data of radiation image is stored in the FPD, sets to enable/disable the retrieving of the image data stored in the FPD and associating of the image data with the patient information of the patient that is currently displayed,
- in a state that an imaging mode switching button was pressed and input, determines whether the pressing input of the imaging mode switching button was an on input to switch to a memory imaging mode,
- in a state that the pressing input of the imaging mode switching button was the on input to a normal imaging mode, performs on setting to the normal imaging mode, and then performs setting to enable a network connection to a communication network, and ends an imaging mode switching processing, and
- in a state that the pressing input of the imaging mode switching button was the on input to the memory imaging mode, performs on setting to the memory imaging mode, and then performs setting to disable the network connection to the communication network, and ends the imaging mode switching processing.

18. The recording medium according to claim 17, wherein the controller is set in advance to an unspecified retrieving mode for retrieving the image data without specifying the patient information of the patient or the order information of the imaging, and in response to an input of an image retrieving button that receives input for retrieving the image data, the controller causes a display to display warning information indicating disabling of retrieving the image data from the image capturer so as to be associated with the at least one of the patient information and the order information that is currently specified.

19. The recording medium according to claim 18, wherein the controller retrieves the image data from the image capturer by the retriever after the warning information is displayed, and the controller causes the display to display an image associating screen for associating the retrieved image data with the at least one of the patient information and the order information in response to completion of retrieving at least one piece of the image data.

20. The recording medium according to claim 17, wherein the computer is caused to further function as a setter that receives a selection input and sets inputted selection, the selection input selecting an unspecified retrieving mode for retrieving the image data without specifying the patient information of the patient or the order information of the imaging or a specified retrieving mode for retrieving the image data from the image capturer so as to be associated with at least one of the patient information and the order information that is currently displayed.

21. A non-transitory recording medium storing a computer readable program causing a computer to function as:
- a retriever that retrieves image data from an image capturer which is an FPD that generates and stores the image data of a medical image; and
- a controller that, in a state in which the image data is to be retrieved without specifying patient information of a patient or order information of imaging, disables retrieving the image data, which is imaged with an imaging method in which the image data is stored in the image capturer without associating at least one of the patient information and the order information with the image data, from the image capturer so as to automatically associate the image data with at least one of the patient information and the order information which is currently specified,
- in a state that a single piece of image data of radiation image is stored in the FPD, sets to enable/disable the retrieving of the image data stored in the FPD and associating of the image data with the patient information of the patient that is currently displayed,
- in a state that an imaging mode switching button was pressed and input, determines whether the pressing input of the imaging mode switching button was an on input to switch to a memory imaging mode,
- in a state that the pressing input of the imaging mode switching button was the on input to a normal imaging mode, performs on setting to the normal imaging mode, and then performs setting to enable a network connection to a communication network, and ends an imaging mode switching processing, and
- in a state that the pressing input of the imaging mode switching button was the on input to the memory imaging mode, performs on setting to the memory imaging mode, and then performs setting to disable the network connection to the communication network, and ends the imaging mode switching processing.

22. The recording medium according to claim 21, wherein the controller is set in advance to an unspecified retrieving mode for retrieving the image data without specifying the patient information of the patient or the order information of the imaging, and
- in response to an input of an image retrieving button that receives input for retrieving the image data, the controller causes a display to display warning information indicating disabling of retrieving the image data from the image capturer so as to be associated with the at least one of the patient information and the order information that is currently specified.

23. The recording medium according to claim 22, wherein the controller retrieves the image data from the image capturer by the retriever after the warning information is displayed, and the controller causes the display to display an image associating screen for associating the retrieved image data with the at least one of the patient information and the order information in response to completion of retrieving at least one piece of the image data.

24. The recording medium according to claim 21, wherein the computer is caused to further function as a setter that receives a selection input and sets inputted selection, the selection input selecting an unspecified retrieving mode for retrieving the image data without specifying the patient information of the patient or the order information of the imaging or a specified retrieving mode for retrieving the image data from the image capturer so as to be associated with at least one of the patient information and the order information that is currently displayed.

\* \* \* \* \*